United States Patent
Olayiwola et al.

(10) Patent No.: US 11,447,704 B2
(45) Date of Patent: *Sep. 20, 2022

(54) OXYGENATE SEPARATION USING A METAL SALT

(71) Applicant: NOVA Chemicals (International) S.A., Fribourg (CH)

(72) Inventors: Bolaji Olayiwola, Calgary (CA); Vasily Simanzhenkov, Calgary (CA); Shahin Goodarznia, Calgary (CA); Michael Koselek, Red Deer (CA); Kamal Serhal, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 257 days.

This patent is subject to a terminal disclaimer.

(21) Appl. No.: 16/597,080

(22) Filed: Oct. 9, 2019

(65) Prior Publication Data

US 2020/0115637 A1 Apr. 16, 2020

Related U.S. Application Data

(60) Provisional application No. 62/744,335, filed on Oct. 11, 2018.

(51) Int. Cl.
*C10G 17/09* (2006.01)
*C07C 7/17* (2006.01)
(Continued)

(52) U.S. Cl.
CPC .............. *C10G 17/09* (2013.01); *C07C 7/005* (2013.01); *C07C 7/17* (2013.01); *C08F 110/02* (2013.01);
(Continued)

(58) Field of Classification Search
None
See application file for complete search history.

(56) References Cited

U.S. PATENT DOCUMENTS

| 3,728,413 A | 4/1973 | Woerner |
| 4,464,189 A | 8/1984 | Tedder |

(Continued)

FOREIGN PATENT DOCUMENTS

| CA | 2907955 A1 | 11/2014 |
| EP | 1676901 | 7/2006 |

(Continued)

OTHER PUBLICATIONS

International Search Report and Written Opinion in International Application No. PCT/IB2019/058602, dated Jan. 8, 2020, 9 pages.

(Continued)

*Primary Examiner* — Tam M Nguyen
(74) *Attorney, Agent, or Firm* — Fish & Richardson P.C.

(57) ABSTRACT

A process, a system, and an apparatus for separation of an oxygenate from a stream is provided. More specifically, a stream comprising the oxygenate is introduced to a quench tower along with a caustic outlet stream comprising a metal salt. Contact between the oxygenate and the metal salt results in conversion of a portion of the oxygenate into a derivative salt. The derivative salt and unconverted oxygenate are condensed by quenching and substantially removed from the quench tower as an oxygenate outlet stream. The gaseous components of the stream, minus a substantial portion of the oxygenate, are removed from the quench tower as a quench outlet stream.

42 Claims, 6 Drawing Sheets

(51) Int. Cl.
  *C07C 7/00*   (2006.01)
  *C08F 110/02* (2006.01)
  *C10G 53/10*  (2006.01)

(52) U.S. Cl.
  CPC ..... *C10G 53/10* (2013.01); *C10G 2300/1092* (2013.01); *C10G 2300/202* (2013.01); *C10G 2300/207* (2013.01); *C10G 2400/20* (2013.01)

(56) References Cited

U.S. PATENT DOCUMENTS

| | | | |
|---|---|---|---|
| 4,899,003 A | 2/1990 | Manyik et al. | |
| 6,037,516 A * | 3/2000 | Morford | C07C 7/148 585/836 |
| 6,166,263 A | 12/2000 | Etzkom et al. | |
| 6,403,854 B1 * | 6/2002 | Miller | B01D 3/143 585/638 |
| 7,005,555 B2 * | 2/2006 | Ding | B01J 8/025 585/638 |
| 7,319,179 B2 | 1/2008 | Lopez Nieto et al. | |
| 7,411,107 B2 | 8/2008 | Lucy | |
| 7,491,843 B2 | 2/2009 | Jobson et al. | |
| 9,993,798 B2 | 6/2018 | Simanzhenkov et al. | |
| 10,427,992 B2 | 10/2019 | Mitkidis et al. | |
| 2004/0102668 A1 * | 5/2004 | Lumgair, Jr. | C10G 3/60 585/638 |
| 2004/0122275 A1 * | 6/2004 | Levin | C07C 7/1485 585/639 |
| 2004/0267069 A1 | 12/2004 | Ding et al. | |
| 2010/0256432 A1 | 10/2010 | Arnold et al. | |
| 2012/0038996 A1 * | 2/2012 | Kura | G03F 7/0007 359/891 |
| 2015/0166440 A1 | 6/2015 | Pavia et al. | |
| 2017/0298281 A1 * | 10/2017 | Weers | C07C 7/14858 |
| 2018/0305278 A1 * | 10/2018 | Serhal | C07C 5/48 |
| 2019/0218161 A1 * | 7/2019 | Simanzhenkov | B08B 9/00 |
| 2019/0315668 A1 | 10/2019 | Raja et al. | |
| 2019/0359546 A1 | 11/2019 | Mamedov | |
| 2020/0157023 A1 * | 5/2020 | Olayiwola | C07C 7/005 |

FOREIGN PATENT DOCUMENTS

| | | | |
|---|---|---|---|
| WO | WO0037399 | 6/2000 | |
| WO | WO0044694 | 8/2000 | |
| WO | WO2015087668 | 6/2015 | |
| WO | WO2017072086 | 5/2017 | |
| WO | WO-2017072086 A1 * | 5/2017 | ............ C07C 51/25 |
| WO | WO2018153831 | 8/2018 | |

OTHER PUBLICATIONS

International Search Report and Written Opinion in International Application No. PCT/IB2019/058604, dated Jan. 7, 2020, 11 pages.
Office Action in U.S. Appl. No. 16/597,156, dated Jul. 23, 2021, 48 pages.
Office Action in U.S. Appl. No. 16/597,156, dated Jun. 23, 2020, 21 pages.
Office Action in U.S. Appl. No. 16/597,156, dated Mar. 11, 2021, 41 pages.

* cited by examiner

OXYGENATE SEPARATION USING A METAL SALT

CROSS REFERENCE TO RELATED APPLICATIONS

This application claims the benefit of the filing date of U.S. Provisional Application No. 62/744,335, which was filed on Oct. 11, 2018. The contents of U.S. Application No. 62/744,335 are incorporated by reference in their entirety as part of this application.

TECHNICAL FIELD

The present disclosure relates generally to separation of oxygenates from lower alkanes using caustic waste.

BACKGROUND

Olefins like ethylene, propylene, and butylene, can be basic building blocks for a variety of commercially valuable polymers. Since naturally occurring sources of olefins may not exist in commercial quantities, polymer producers may rely on methods for converting the more abundant lower alkanes into olefins. Typically, a polymer producer can utilize steam cracking to produce alkenes from the lower alkanes. Steam cracking is a highly endothermic process where steam-diluted lower alkanes are subjected very briefly to a high temperature of at least 700° C. which requires a high energy demand. Additionally, steam cracking can cause coke formation in the reactor which can lead to increased maintenance costs and decreased profitability.

Oxidative dehydrogenation (ODH) is an alternative to steam cracking that can be exothermic, can have a low energy demand, and can produce little or no coke. In ODH, a lower alkane is mixed with oxygen in the presence of a catalyst and optionally an inert diluent at low temperatures such as, for example 300° C., to produce the corresponding alkene. In some examples, various other by-products such as, for example, carbon monoxide, carbon dioxide, and an oxygenate may also be produced in the ODH process. The by-products may be subject to further processing prior to being a marketable product or may be disposed of. The additional processing for separation of by-products from the marketable product can increase the complexity of a chemical complex and associated energy demands.

Additional processing downstream of the ODH process includes removal of oxygenates, such as acetic acid, using a quench tower, followed by removal of carbon oxides, particularly carbon dioxide, using an amine tower or caustic wash, or both. Oxygenates removed from the quench tower using a quench tower results in dilute solutions of the oxygenate that may require further processing to be marketable. Use of a caustic wash to remove carbon oxides produces spent caustics, or metal salts such as sodium carbonate or sodium hydrogen sulfide, which need to be disposed of using deep well injection, wet air oxidation, or incineration. This disclosure relates to use of the metal salts to simplify separation and concentration of oxygenates present in and removed from a gaseous stream.

SUMMARY

In one aspect, a method for separation of an oxygenate from a stream is provided. More specifically, the stream comprising the oxygenate is introduced to a quench tower along with a caustic outlet stream comprising a metal salt. The streams are quenched with addition of water and contact between the oxygenate and the metal salt during quenching facilitates conversion of the oxygenate into a derivative salt. An oxygenate outlet stream comprising a substantial portion of the derivative salt and at least a substantial portion of unconverted oxygenate is removed from the quench tower. A quench outlet stream, comprising gaseous components present in the stream, is also removed from the quench tower.

In yet another aspect, an apparatus for separation of an oxygenate from a stream is provided. More specifically, the apparatus comprises a quench tower comprising a quench inlet, a quench outlet, a metal salt inlet, and an oxygenate outlet. The quench inlet is configured to receive the stream comprising the oxygenate. The metal salt inlet is configured to receive into the quench tower a caustic outlet stream comprising a metal salt, allowing contact of the caustic outlet stream with the stream. The quench outlet is suitable for removing a quench outlet stream and the oxygenate outlet is suitable for removing an oxygenate outlet stream comprising at least a substantial portion of a derivative salt formed by contact of the oxygenate with the metal salt and at least a substantial portion of the unconverted oxygenate.

In yet another aspect, a system for separation of an oxygenate from a stream is provided. More specifically, the system comprises a quench tower configured to receive a stream comprising the oxygenate and a caustic outlet stream comprising a metal salt resulting in contact of the oxygenate with the metal salt and conversion of a portion of the oxygenate into a derivative salt, quench the stream and the caustic outlet stream, remove at least a substantial portion of a derivative salt and at least a substantial portion of the unconverted oxygenate, and remove an quench outlet stream comprising gaseous components of the stream.

In one aspect, a method is provided to convert a lower alkane to an alkene. More specifically, an input stream comprising oxygen and the lower alkane is introduced to an oxidative dehydrogenation (ODH) reactor. At least a portion of the lower alkane is converted to the alkene in the ODH reactor and an ODH outlet stream comprising the alkene, an oxygenate, and a carbon-based oxide is produced. The ODH outlet stream and a caustic outlet stream comprising a metal salt are in introduced to a quench tower and quenched. Contact in the quench tower between the oxygenate and the metal salt facilitates conversion of a portion of the oxygenate into a derivative salt. A quench outlet stream comprising at least a substantial portion of the alkene and at least a substantial portion of the carbon-based oxide is removed from the quench tower, as is an oxygenate outlet stream comprising at least a substantial portion of the unconverted oxygenate and at least a substantial portion of the derivative salt. The quench outlet stream is introduced to a caustic wash tower and contacted with a caustic agent in the caustic wash tower to form a metal salt that is removed from the caustic tower and may recycled and used as part of the caustic outlet stream introduced into the quench tower with the ODH outlet stream.

In another aspect, an apparatus is provided for oxidative dehydrogenation (ODH) of a lower alkane to an alkene. More specifically, the apparatus comprises an ODH reactor, a quench tower, a caustic wash tower, and a return line. The ODH reactor comprises an ODH inlet and an ODH outlet. The ODH inlet is suitable for transporting an ODH inlet stream comprising the lower alkane into the ODH reactor. The ODH outlet is suitable for transporting an ODH outlet stream comprising the alkene, an oxygenate, and a carbon-based oxide. The quench tower comprises a quench inlet, a quench outlet, a metal salt inlet, and an oxygenate outlet. The quench inlet is in fluid communication with the ODH outlet to receive the ODH outlet stream. The quench outlet is suitable for transporting a quench outlet stream comprising at least a substantial portion of the alkene and at least a substantial portion of the carbon-based oxide. The oxygenate outlet is suitable for transporting an oxygenate outlet stream comprising at least a substantial portion of the oxygenate and a derivative salt. The caustic wash tower comprises a wash inlet, a wash outlet, a caustic inlet, and a caustic outlet. The wash inlet is in fluid communication with the quench outlet to receive the quench outlet stream. The caustic outlet is suitable for transporting a caustic outlet stream comprising a metal salt. The return line is in fluid communication with the caustic outlet to receive the caustic outlet stream and output the caustic outlet stream into the metal salt inlet of the quench tower.

In another aspect, a system is provided for oxidative dehydrogenation (ODH) of a lower alkane. More specifically, the system comprises an ODH reactor, a quench tower, a caustic wash tower, and a return line. The ODH reactor is configured to receive an input stream comprising oxygen and the lower alkane. The ODH reactor is configured to produce an ODH outlet stream comprising an alkene, an oxygenate, and a carbon-based oxide. The quench tower is configured to receive and quench the ODH outlet stream and a caustic outlet stream comprising a metal salt, contact the oxygenate with the metal salt to convert a portion of the oxygenate to a derivative salt, remove an oxygenate outlet stream comprising at least a substantial portion of the unconverted oxygenate and at least a substantial portion of the derivative salt, and produce a quench outlet stream comprising at least a substantial portion of the alkene and at least a substantial portion of the carbon-based oxide. The caustic wash tower is configured to receive the quench outlet stream and contact a substantial portion of the carbon-based oxide from the quench outlet stream with a caustic agent to form a caustic outlet stream comprising a metal salt. The return line is configured to direct the caustic outlet stream into the quench tower and contact the caustic outlet stream with the ODH outlet stream to form a derivative salt from the metal salt and the oxygenate. The oxygenate outlet stream comprises a substantial portion of the derivative salt.

It is understood that the inventions described in this specification are not limited to the examples summarized in this Summary. Various other aspects are described and exemplified herein.

BRIEF DESCRIPTION OF THE DRAWINGS

The features and advantages of the examples, and the manner of attaining them, will become more apparent and the examples will be better understood by reference to the following description of examples taken in conjunction with the accompanying drawings, wherein.

DETAILED DESCRIPTION

Figure 1:
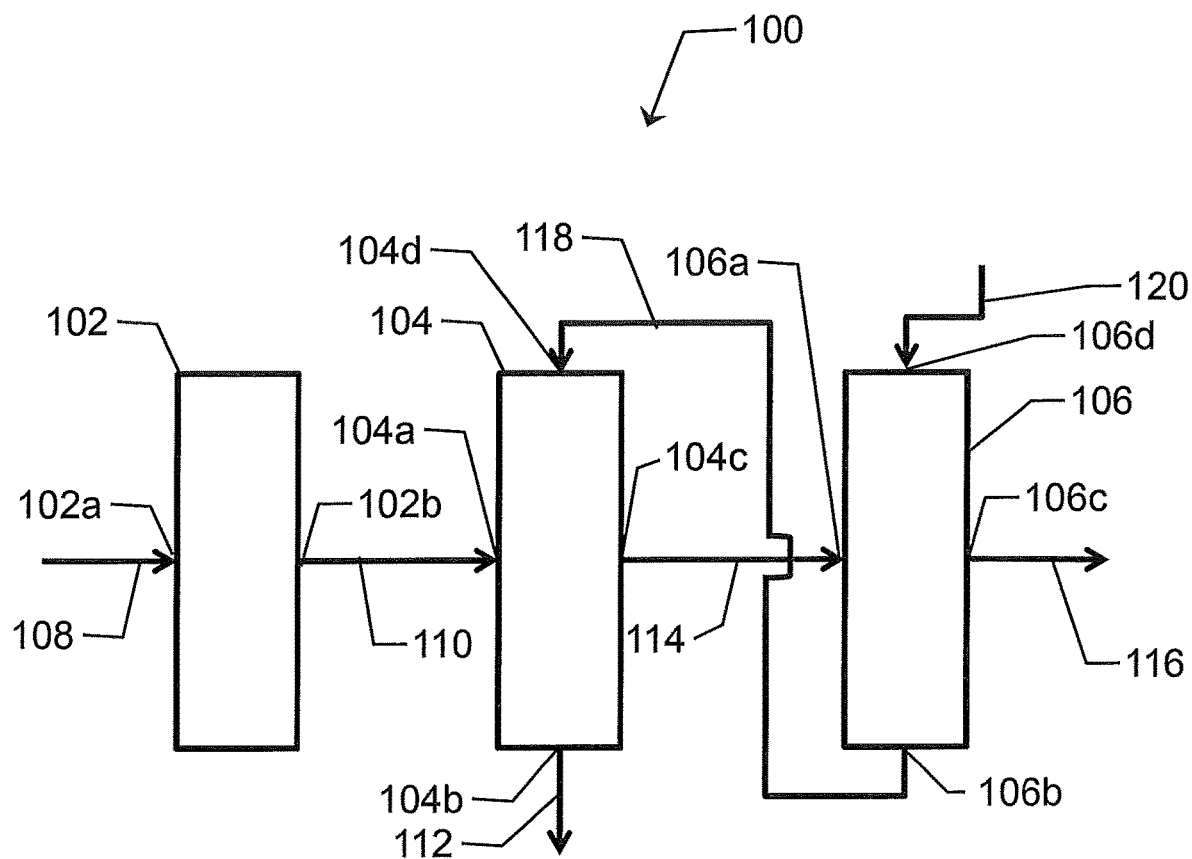
FIG. 1 is a flow diagram illustrating a non-limiting example of a system to convert an alkane to an alkene.

The exemplifications set out herein illustrate certain examples, in one form, and such exemplifications are not to be construed as limiting the scope of the examples in any manner.

Certain exemplary aspects of the present disclosure will now be described to provide an overall understanding of the principles of the structure, function, manufacture, and use of the systems, apparatus, and methods disclosed herein. One or more examples of these aspects are illustrated in the accompanying drawings. Those of ordinary skill in the art will understand that the systems and methods specifically described herein and illustrated in the accompanying drawings are non-limiting exemplary aspects and that the scope of the various examples of the present invention is defined solely by the claims. The features illustrated or described in connection with one exemplary aspect may be combined with the features of other aspects. Such modifications and variations are intended to be included within the scope of the present invention.

Reference throughout the specification to "various examples," "some examples," "one example," or "an example", or the like, means that a particular feature, structure, or characteristic described in connection with the example is included in at least one example. Thus, appearances of the phrases "in various examples," "in some examples," "in one example", or "in an example", or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features structures, or characteristics of one or more other examples without limitation. Such modifications and variations are intended to be included within the scope of the present examples.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the desired properties, which the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

The grammatical articles "a", "an", and "the", as used herein, are intended to include "at least one" or "one or more", unless otherwise indicated, even if "at least one" or "one or more" is expressly used in certain instances. Thus, the foregoing grammatical articles are used herein to refer to one or more than one (i.e., to "at least one") of the particular identified elements. Further, the use of a singular noun includes the plural, and the use of a plural noun includes the singular, unless the context of the usage requires otherwise.

As used herein, the term "substantial portion" means at least 50 percent by weight. A substantial portion can be 50% to 100% by weight such as, for example, at least 60% by weight, at least 70% by weight, at least 80% by weight, at least 90% by weight, or at least 95% by weight.

As used herein, the term "alkane" refers to an acyclic saturated hydrocarbon. In various examples, an alkane consists of hydrogen and carbon atoms arranged in a linear structure in which all of the carbon-carbon bonds are single bonds. An alkane has the general chemical formula $C_nH_{2n+2}$ and in various examples, for a lower alkane, 'n' is in a range of 2 to 4. In various examples, an alkane refers to one or more of ethane, propane, butane, pentane, hexane, octane, decane and dodecane. In various examples, a lower alkane refers to one or more of ethane, propane, and butane.

As used herein, the term "alkene" refers to an unsaturated hydrocarbon that contains at least one carbon—carbon double bond. In various examples, alkene refers to alpha olefins. For example, alkene can refer to one or more of ethylene, propylene, 1-butene, butadiene, pentene, pentadiene hexene, octene, decene, and dodecene.

As used herein, the terms "alpha olefin" or "α-olefin" refer to a family of organic compounds which are an alkene (also known as olefin) with a chemical formula $C_xH_{2x}$, distinguished by having a double bond at the primary or alpha (α) position. In various examples, alpha olefin refers to one or more of ethylene, propylene, 1-butene, 1-pentene, 1-hexene, 1-octene, 1-decene, and 1-dodecene.

As used herein, the term "fixed bed reactor" refers to one or more reactors, in series or parallel, often including a cylindrical tube filled with catalyst pellets with reactants flowing through the bed and being converted into products. The catalyst in the reactor may have multiple configurations including, for example, one large bed, several horizontal beds, several parallel packed tubes, multiple beds in their own shells, and/or combinations thereof.

As used herein, the term "fluidized bed reactor" refers to one or more reactors, in series or parallel, often including a fluid (e.g., gas or liquid) which can be passed through a solid granular catalyst, which can be shaped as tiny spheres, at a velocity high enough to suspend the solid granular catalyst and cause the solid granular catalyst to behave like a fluid.

As used herein, the tend "HDPE" refers to high density polyethylene, which generally has a density of greater or equal to 0.941 g/cm$^3$. HDPE has a low degree of branching HDPE can be often produced using chromium/silica catalysts, Ziegler-Natta catalysts or metallocene catalysts.

As used herein, the term "LDPE" refers to low density polyethylene, which can be a polyethylene with a high degree of branching with long chains. Often, the density of a LDPE will range from 0.910-0.940 g/cm$^3$. LDPE can be created by free radical polymerization.

As used herein, the term "LLDPE" refers to linear low density polyethylene, which can be a polyethylene that can have significant numbers of short branches resulting from copolymerization of ethylene with at least one α-olefin comonomer. In some examples, LLDPE has a density in the range of 0.915-0.925 g/cm$^3$. In some examples, the LLDPE can be an ethylene hexene copolymer, ethylene octene copolymer, or ethylene butene copolymer. The amount of comonomer incorporated can be from 0.5 mole % to 12 mole % relative to ethylene, in some examples from 1.5 mole % to 10 mole %, and in other examples from 2 mole % to 8 mole %.

As used herein, the term "MDPE" refers to medium density polyethylene, which can be a polyethylene with some short and/or long chain branching and a density in the range of 0.926-0.940 g/cm$^3$. MDPE can be produced using chromium/silica catalysts, Ziegler-Natta catalysts or metallocene catalysts.

As used herein, the term "VLDPE" refers to very low density polyethylene, which can be a polyethylene with high levels of short chain branching with a typical density in the range of 0.880-0.915 g/cc. In some examples, VLDPE can be a substantially linear polymer. VLDPE can be typically produced by copolymerization of ethylene with α-olefins. VLDPE can be produced using metallocene catalysts.

As used herein, the term "gas phase polyethylene process" refers to a process where a mixture of ethylene, optional alpha olefin comonomers, and hydrogen can be passed over a catalyst in a fixed or fluidized bed reactor. The ethylene and optional alpha olefins polymerize to form grains of polyethylene, suspended in the flowing gas, which can pass out of the reactor. In various examples, two or more of the individual reactors are placed in parallel or in series, each of which are under slightly different conditions, so that the properties of different polyethylenes from the reactors are present in the resulting polyethylene blend. In some examples, the catalyst system includes, for example, chromium catalysts, Ziegler-Natta catalysts, zirconocene catalysts, and metallocene catalysts and combinations thereof.

As used herein, the term "high pressure polyethylene process" refers to converting ethylene gas into a white solid by heating it at very high pressures in the presence of minute quantities of oxygen (less than 10 ppm oxygen) at 1000 bar-3000 bar and at 80° C.-300° C. In some examples, the high pressure polyethylene process produces LDPE.

As used herein, the term "low pressure polyethylene process" refers to polymerizing ethylene using a catalyst that in some examples includes aluminum at generally lower pressures than the high pressure polyethylene process. In some examples, the low pressure polyethylene process can be carried out at 10 bar-80 bar and at 70° C.-300° C. In various examples, the low pressure polyethylene process provides HDPE. In various examples, an α-olefin comonomer can be included in the low pressure polyethylene process to provide LLDPE.

As used herein, the term "solution polyethylene process" refers to processes that polymerize ethylene and one or more optional α-olefins in a mixture of lower alkane hydrocarbons in the presence of one or more catalysts. In various examples, two or more of the individual reactors can be placed in parallel or in series, each of which can be under slightly different conditions, so that the properties of different polyethylenes from the reactors are present in the resulting polyethylene blend. In some examples the catalysts include, but are not limited to, chromium catalysts, Ziegler- Natta catalysts, zirconocene catalysts, hafnocene catalysts, phosphaimine catalysts, metallocene catalysts, and combinations thereof.

As used herein, the term "slurry polyethylene process" refers to single-tube loop reactors, double-tube loop reactors or autoclaves (stirred-tank reactors) used to polymerize ethylene and optional α-olefins in the presence of a catalyst system and a diluent. Non-limiting examples of diluents include isobutane, n-hexane, or n-heptane. In some examples, two or more of the individual reactors are placed in parallel or in series, each of which can be under slightly different conditions, so that the properties of different polyethylenes from the reactors are present in the resulting polyethylene blend. In some examples, the catalyst system includes, for example, chromium catalysts, Ziegler-Natta catalysts, zirconocene catalysts, hafnocene catalysts, phosphaimine catalysts, metallocene catalysts, and combinations thereof.

As used herein, the term "long chain branching" refers to a situation where during α-olefin polymerization, a vinyl terminated polymer chain can be incorporated into a growing polymer chain. Long branches often have a length that can be longer than the average critical entanglement distance of a linear (e.g., no long chain branching) polymer chain. In some examples, long chain branching effects melt rheological behavior.

As used herein, the term "short chain branching" refers to a copolymer of ethylene with an α-olefin or with branches of less than 40 carbon atoms. In some examples, the α-olefin or branches are present at less than 20% by weight of the polyethylene, in some examples less than 15% by weight. In some examples, the presence of short chain branches can interfere with the formation of the polyethylene crystal structure and can be observed as a lower density compared with a linear (no short chain branching) polyethylene of the same molecular weight.

As used herein, the term "monomer" refers to small molecules containing at least one double bond that can react in the presence of a free radical polymerization initiator to become chemically bonded to other monomers to form a polymer.

As used herein, the term, "olefinic monomer" includes, without limitation, α-olefins, and in some examples, ethylene, propylene, 1-butene, 1-hexene, 1-octene, and combinations thereof.

As used herein, the term "polyolefin" refers to a material, which is prepared by polymerizing a monomer composition containing at least one olefinic monomer.

As used herein, the term "polyethylene" can include, for example, a homopolymer of ethylene, a copolymer of ethylene, and an α-olefin.

As used herein, the term "polypropylene" can include a homopolymer of propylene such as, for example, isotactic polypropylene and syndiotactic polypropylene, a copolymer of propylene, and an α-olefin.

As used herein, the term "polymer" refers to macromolecules composed of repeating structural units connected by covalent chemical bonds and can include, for example, a homopolymer, a random copolymer, a block copolymer, and a graft copolymer.

As used herein, the term "thermoplastic" refers to a class of polymers that can soften or become liquid when heated and can harden when cooled. In some examples, a thermoplastic can be a high-molecular-weight polymer that can be repeatedly heated and remolded. In various examples, a thermoplastic resin can include a polyolefin and an elastomer that has thermoplastic properties.

As used herein, the terms "thermoplastic elastomers" and "TPE" refer to a class of copolymers or a blend of polymers (in some examples a blend of a thermoplastic and a rubber) which includes materials having both thermoplastic and elastomeric properties.

As used herein, the terms "thermoplastic olefin" or "TPO" refer to polymer/filler blends that contain some fraction of polyethylene, polypropylene, block copolymers of polypropylene, rubber, and a reinforcing filler. The fillers can include, for example, talc, fiberglass, carbon fiber, wollastonite, metal oxy sulfate, and combinations thereof. The rubber can include, for example, ethylene-propylene rubber, EPDM (ethylene-propylene-diene rubber), ethylene-butadiene copolymer, styrene-ethylene-butadiene-styrene block copolymers, styrene-butadiene copolymers, ethylene-vinyl acetate copolymers, ethylene-alkyl (meth)acrylate copolymers, and VLDPE such as those available under the Flexomer® resin trade name from the Dow Chemical Co., Midland, Mich., styrene-ethylene-ethylene-propylene-styrene (SEEPS). These can also be used as the materials to be modified by the interpolymer to tailor their rheological properties.

Unless otherwise specified, all molecular weight values are determined using gel permeation chromatography (GPC). Molecular weights are expressed as polyethylene equivalents with a relative standard deviation of 2.9% for the number average molecular weight ("Mn") and 5.0% for the weight average molecular weight ("Mw"). Unless otherwise indicated, the molecular weight values indicated herein are weight average molecular weights (Mw).

Unless otherwise specified, all pressure values are gauge pressure values.

As used herein, the term "apparatus" refers to at least one of a device, a machine, a structure, and other suitable equipment that can carry out the functions of the method, the apparatus, and the system according to the present disclosure. For example, the term "apparatus" can be a chemical complex, and the terms are interchangeable.

Many chemical production processes can have a co-product of an oxygenate such as, for example, acetic acid, acrylic acid, maleic acid, and maleic anhydride. A quench tower is typically used for removing the oxygenate from a process stream. In the quench tower a quenching agent can condense the oxygenate in the process stream while an unreacted hydrocarbon and a carbon-based oxide or a sulfide can be in a gas state. This can enable separation of the condensed oxygenate from the gaseous components. In some quenching processes, the oxygenate can be diluted to a low concentration that may be insufficient for subsequent applications.

The oxygenate can require purification and/or further processing in order to generate a product sufficient for subsequent applications. For example, water may have to be removed from the oxygenate to increase the concentration of the oxygenate. Separation of the oxygenate from water can increase the complexity of a quench tower and/or a separation vessel due to the small thermal (e.g., boiling point) separation between the oxygenate and the water. In various examples, a mixture of oxygenate and water can be azeotropic. The separation vessel may employ a large column, a high quantity of stages, a high reflux ratio, and a high energy demand to separate an azeotropic mixture of oxygenate and water.

In the petrochemical industry, a process stream can be treated with a caustic agent in order to remove a contaminant. For example, during the processing of gasoline, kerosene, and liquified petroleum gas (LPG), sulfides and organic acids are removed by treatment with a caustic agent such as sodium hydroxide. In an ethane cracking process carbon dioxide can be removed using a caustic agent. The treatment can comprise reacting the caustic agent with the contaminate to form a different product which can be removed from the process stream. For example, reacting gaseous hydrogen sulfide with a solution of caustic sodium hydroxide can produce water and sodium hydrogen sulfide which can be removed in the liquid state with the water. In the case of an ethane cracker, carbon dioxide can be removed from the process stream by conversion of the carbon dioxide to sodium bicarbonate in the caustic tower.

Upon reacting the caustic agent with the contaminate, the caustic agent becomes consumed (e.g., spent). The spent caustic may be undesirable and may require disposal which can be costly and increase complexity of the chemical production process. For example, the spent caustic can be sold to pulp and paper manufacturers which may require hauling of the spent caustic to a different facility. Spent caustic can also be disposed by deep well injection, incineration, and/or neutralized by wet air oxidation. These disposal processes can require additional energy, cost, and complexity in the chemical production process.

Converting the spent caustic to a marketable product which can remove the oxygenate from the process stream can lower energy requirements, cost, and complexity of a chemical production process. Thus, a method, a system, and an apparatus are provided which can enhance the purification of the oxygenate and reduce energy requirements for the purification. More specifically, a stream comprising the oxygenate can be introduced to a quench tower and the oxygenate can be removed from the stream. A caustic outlet stream comprising a metal salt can be introduced to the quench tower. The stream can be contacted with the caustic outlet stream to form a derivative salt from the metal salt and the oxygenate. A quench outlet stream can be produced in the quench tower and an oxygenate outlet stream comprising at least a substantial portion of the oxygenate and at least a substantial portion of the derivative salt can be produced in the quench tower.

Oxidative dehydrogenation (ODH) can couple the endothermic dehydrogenation of an alkane with the strongly exothermic oxidation of hydrogen. For example, ODH of an alkane can comprise contacting an alkane and oxygen in an ODH reactor with an ODH catalyst under reaction conditions (e.g., temperature, pressure, flow rate, etc.) that can promote oxidation of the alkane into the corresponding alkene. The corresponding alkene includes hydrocarbons with the same number of carbons as the alkane used in the ODH reactor, but with the addition of one carbon to carbon double bond. For example, utilizing ODH, ethane can be converted to ethylene, propane can be converted to propylene, and butane can be converted to butylene.

Any ODH catalyst known in the art can be suitable for use with the present disclosure. For example, an ODH catalyst containing a mixed metal oxide can be used. Additionally, reaction conditions can be controlled to adjust the selectivity and yield of the ODH reactor products. As known in the art, conditions will vary and can be optimized for a particular alkane, for a specific catalyst, a select product, and/or a particular inert diluent. A co-product of an ODH reaction can be an oxygenate which may need to be removed from the process stream and the ODH process may generate spent caustic.

Thus, in various examples, a method, a system, and an apparatus are provided for converting a lower alkane to an alkene. An input stream comprising oxygen and the lower alkane can be introduced to an ODH reactor. At least a portion of the lower alkane can be converted to the alkene in the ODH reactor and an ODH outlet stream comprising the alkene and an oxygenate, and a carbon-based oxide can be produced. The ODH outlet stream can be introduced to a quench tower and the oxygenate can be removed from the ODH outlet stream. A quench outlet stream comprising at least a substantial portion of the alkene and at least a substantial portion of the carbon-based oxide can be produced in the quench tower. Additionally, an oxygenate outlet stream comprising at least a substantial portion of the oxygenate can be produced in the quench tower. The quench outlet stream can be introduced to a caustic wash tower. The quench outlet stream can be contacted with a caustic agent in the caustic wash tower to form a caustic outlet stream comprising a metal salt. The caustic outlet stream can be introduced to the quench tower. The ODH outlet stream can be contacted with the caustic outlet stream to form a derivative salt from the metal salt and the oxygenate. The oxygenate outlet stream can comprise a substantial portion of the derivative salt.

Referring to FIG. 1, illustrated is a flow diagram of a non-limiting example of a system 100 to convert an alkane to an alkene. As illustrated, an ODH reactor 102 and a quench tower 104 can be in operative communication. For example, an ODH outlet 102b of the ODH reactor 102 can be in fluid communication with a quench inlet 104a of the quench tower 104 via an ODH outlet line 110. Additionally, a quench outlet 104c of the quench tower 104 can be in fluid communication with a wash inlet 106a of the caustic wash tower 106 via a quench outlet line 114. Accordingly, the ODH reactor 102 can be in fluid communication with the caustic wash tower 106 via the quench tower 104.

The ODH reactor 102 can comprise an ODH inlet 102a which can be configured to receive an ODH inlet stream from an ODH inlet line 108 and can be suitable to transport the ODH inlet stream into the ODH reactor 102. The ODH inlet stream can comprise a gaseous mixture of a lower alkane and oxygen. In various examples, the ODH inlet stream additionally can include at least one of a carbon-based oxide, a sulfide, steam, and an inert diluent. In various examples, the ODH inlet stream can comprise another hydrocarbon such as, for example, methane. The inert diluent can comprise, for example, nitrogen. In various examples, the carbon-based oxide can comprise at least one of carbon dioxide and carbon monoxide. The concentration of the oxygen and the lower alkane within the mixture in the ODH inlet stream and the temperature and pressure of the ODH inlet stream can be adjusted such that the mixture can be outside of the flammability limits of the mixture. In various examples, the lower alkane is in a gas state. In various examples, the carbon-based oxide is in a gas state. In various examples, the sulfide is in a gas state.

In various examples, there may be multiple ODH inlet lines configured to introduce the ODH inlet stream to the ODH reactor 102. For example, each reactant (e.g., lower alkane, oxygen, steam, carbon-based oxide, and inert diluent) may be added directly to the ODH reactor 102, each in separate inlet lines (not shown). Alternatively, one or more reactants may be pre-mixed and added in more than one inlet line. In various example, reactants may be mixed together prior to the ODH reactor 102 and subsequently introduced into the ODH reactor in a common ODH inlet. In various examples, steam may be added indirectly as water mixed with an additional reactant and the resulting mixture can be preheated before entering the ODH reactor 102. When adding steam indirectly as water, the preheating process can increase the temperature of the mixture so that the water can be substantially converted, and in various examples fully converted, to steam before entering the ODH reactor 102.

The ODH reactor 102 can include a catalyst capable of catalyzing the conversion of the reactants within the ODH inlet stream to products such as, for example, an alkene and an oxygenate and in various examples, a carbon-based oxide. The catalyst may be, for example, a mixed metal oxide catalyst, many varieties of which have been described in the art. In various examples, the products may additionally include water.

As known in the art, the catalyst composition, the composition of the ODH inlet stream, and reaction conditions within the ODH reactor 102, such as temperature and pressure, can be adjusted in order to promote selectivity, as desired, of a product. For example, the ratio of the lower alkane to oxygen can be outside of the upper flammability limit of the mixture. In various examples, the oxygen concentration in the ODH inlet stream can be in a range of 0.1% to 30% by weight of the ODH inlet stream, and in some examples range from 0.1% to less than 30% by weight, less than 25% by weight, or less than 20% by weight. In various examples, the lower alkane concentration in the ODH inlet stream can range from 0.1% to 50% by weight of the ODH inlet stream, and in some examples range from 0.1% to less than 50% by weight or less than 40% by weight.

In various examples increasing the steam concentration in the ODH inlet stream can increase the amount of oxygenate produced relative to the alkene produced in the ODH reactor 102. In various examples, reducing the steam concentration in the ODH inlet stream can decrease the amount of oxygenate produced relative to the alkene produced in the ODH reactor 102. The concentration of steam in the ODH inlet stream can be in a range of 0.1% to 40% by weight of the total ODH inlet stream 108, and in some examples range from 0.1% to less than 40% by weight, or less than 25% by weight. In various examples, the concentration of the stream in the ODH inlet stream can be at least 1% by weight. In various examples, the ODH inlet stream can comprise 20% oxygen by weight, 40% lower alkane by weight, and the balance being steam, carbon dioxide, and/or an inert diluent.

In various examples, the ODH process has a selectivity for the corresponding alkene (e.g., ethylene in the case of ethane ODH) of greater than 95% such as, for example, greater than 98%. The gas hourly space velocity (GHSV) within the ODH reactor 102 can be from 500 to 30000 $h^{-1}$ and in some examples the GHSV within the ODH reactor 102 can be greater than 1000 $h^{-1}$. In various examples, the space-time yield of corresponding alkene (e.g., productivity) in grams(g)/hour per kilogram (kg) of the catalyst can be at least 900 such as, for example, greater than 1500, greater than 3000, or greater than 3500, at an ODH reactor temperature of, for example, 350° C. to 400° C. In various examples, the productivity of the catalyst can increase with increasing temperature in the ODH reactor 102 until the selectivity of the alkene decreases.

Use of an ODH reactor for performing an ODH reaction consistent with the disclosure falls within the knowledge of the person skilled in the art. In various examples, the reaction can be conducted at temperatures in a range of 300° C. to 450° C. such as, for example, 300° C. to 425° C., or 330° C. to 400° C. In various examples, the reaction can be conducted at pressures in a range of 0.5 pounds per square inch (psi) to 100 psi (3.447 to 689.47 kPa) such as, for example, 15 psi to 50 psi (103.4 to 344.73 kPa). In various examples, the lower alkane can have a residence time in the ODH reactor 102 in a range of 0.002 seconds (s) to 30 s, or from 1 s to 10 s.

The products of the ODH reaction can leave the ODH reactor 102 through the ODH outlet 102b in an ODH outlet stream. The ODH outlet 102b can be configured to receive the ODH outlet stream and can be suitable to transport the ODH outlet stream 110 out of the ODH reactor 102 and into the ODH outlet line 110. In various examples, in addition to the products, the ODH outlet stream can include unreacted components from the ODH inlet stream such as, for example, lower alkane, carbon-based oxide, oxygen, steam, inert diluent, and combinations thereof. In various examples, the temperature of the ODH outlet stream can be in a range of 100° C. to 450° C., such as for example, 300° C. to 425° C., and in certain examples 330° C. to 400° C.

Any of the known reactor types applicable for the ODH of an alkane may be used with the present disclosure. For example, a fixed bed reactor, a fluidized bed reactor, or combinations thereof can be used for the ODH reactor 102. In a typical fixed bed reactor, reactants are introduced into the reactor at an inlet and flow past an immobilized catalyst. Products are formed and leave through the outlet of the reactor. A person skilled in the art would understand which features are required with respect to shape and dimensions of the reactor, inputs for reactants, outputs for products, temperature and pressure control, and means for immobilizing the catalyst.

In a typical fluidized bed reactor, the catalyst bed can be supported by a porous structure or a distributor plate and located near a lower end of the reactor. Reactants flow through the fluidized bed reactor at a velocity sufficient to fluidize the bed (e.g., the catalyst rises and begins to swirl around in a fluidized manner). The reactants can be converted to products upon contact with the fluidized catalyst and the reactants are subsequently removed from an upper end of the reactor. A person of ordinary skill in the art would understand which features are required with respect to shape and dimensions of the reactor, the shape and size of the distributor plate, the input temperature, the output temperature, the reactor temperature and pressure, inputs for reactors, outputs for reactants, and velocities to achieve fluidization.

In various examples, there may be multiple ODH reactors connected in series or in parallel. Each ODH reactor may be the same or different. For example, each ODH reactor can contain the same or different ODH catalyst. In various examples, the multiple ODH reactors can each be a fixed bed reactor, can each be a fluidized bed reactor, or the multiple ODH reactors can be combinations of fixed bed reactors and fluidized bed reactors.

Regardless of the configuration of the ODH reactor 102, the ODH outlet 102b can be in fluid communication with the quench inlet 104a of the quench tower 104 via the ODH outlet line 110 to direct the ODH outlet stream to the quench tower 104. The quench inlet 104a can be configured to receive the ODH outlet stream from the ODH outlet line 110 and can be suitable to transport the ODH outlet stream into the quench tower 104. In various examples, the quench inlet 104a can be configured to receive a product stream and can be suitable to transport the product stream into the quench tower 104. The product stream can comprise at least one of a hydrocarbon, such as, for example, an alkane or an alkene, and an organic alcohol, such as, for example, ethanol.

The quench tower 104 can comprise a flash drum, an oxygenate scrubber, the like, or combinations thereof. The quench tower 104 can be configured to quench the components in the ODH outlet stream and remove at least a substantial portion of the alkene from the ODH outlet stream. In various examples, the quench tower 104 can facilitate the removal of oxygenate and water from the ODH outlet stream. The quench tower 104 can produce a quench outlet stream comprising at least a substantial portion of the alkene from the ODH outlet stream and in various examples, at least a substantial portion of the carbon-based oxide from the ODH outlet stream. In various examples, the quench outlet stream can comprise additional components from the ODH outlet stream such as, for example, a portion of the oxygen, a portion of the oxygenate, a portion of the inert diluent, a portion of the steam, and a portion of the unreacted alkane. In various examples, the quench outlet stream is in a gas state. The quench outlet stream exits the quench tower 104 through the quench outlet 104c. The quench outlet 104c can be configured to receive the quench outlet stream and can be suitable to transport the quench outlet stream out of the quench tower 104 into the quench outlet line 114.

The quench tower 104 can produce an oxygenate outlet stream comprising at least a substantial portion of the oxygenate from the ODH outlet stream and in some examples, a derivative salt as discussed herein. In various examples, the oxygenate outlet stream can comprise additional components from the ODH outlet stream such as, for example, a substantial portion of the water (e.g., steam), lower alkane, alkene, oxygen, and carbon-based oxide. The oxygenate outlet stream can exit the quench tower 104 through an oxygenate outlet 104b of the quench tower 104. The oxygenate outlet 104b can be configured to receive the oxygenate outlet stream and can be suitable to transport the oxygenate outlet stream out of the quench tower 104 into the oxygenate outlet line 112.

In various examples, the quench tower 104 can be in operative communication with a caustic wash tower 106. The quench outlet 104c can be in fluid communication with the wash inlet 106a of the caustic wash tower 106 via the quench outlet line 114 to direct the quench outlet stream to the caustic wash tower 106. The wash inlet 106a can be configured to receive the quench outlet stream from the quench outlet line 114 and can be suitable to transport the quench outlet stream into the caustic wash tower 106.

The caustic wash tower 106 can comprise the wash inlet 106a, a wash outlet 106c, a caustic inlet 106d, and a caustic outlet 106b. The caustic inlet 106d can be configured to receive a caustic agent stream comprising a caustic agent from a caustic agent line 120 and can be suitable to transport the caustic agent stream into the caustic wash tower 106. The caustic agent can comprise a hydroxide, such as, for example, at least one of sodium hydroxide, potassium hydroxide, and ammonia hydroxide. In various examples, the caustic agent stream includes water or any other suitable component.

The caustic wash tower 106 can be configured to contact the caustic agent stream with the quench outlet stream. In various examples comprising a carbon-based oxide comprising carbon dioxide, the caustic agent can react with carbon dioxide and/or sulfide in the quench outlet stream to form a metal salt. The metal salt may be, for example, at least one of a sulfide and a carbonate. The carbonate can comprise at least one of sodium bicarbonate, potassium carbonate, and ammonium bicarbonate. The sulfide can comprise hydrogen sulfide. In various examples, the metal salt can be water soluble. The reaction can remove at least a substantial portion of the carbon-based oxide (e.g., carbon dioxide), and in various examples the sulfide (e.g., hydrogen sulfide), from the quench outlet stream and produce a wash outlet stream and a caustic outlet stream. For example, the reaction of sodium hydroxide and carbon dioxide is shown in Scheme 1.

Scheme 1

The wash outlet stream can comprise unreacted components from the quench outlet stream. The wash outlet 106c can be configured to receive the wash outlet stream and can be suitable to transport the wash outlet stream out of the caustic wash tower 106 into the wash outlet line 116.

The caustic outlet stream can comprise a substantial portion of the metal salt and in some examples, at least one of water, caustic agent, and oxygenate. In various examples, the caustic outlet 106b can be configured to receive the caustic outlet stream and can be suitable to transport the caustic outlet stream into a return line 118. The return line 118 can be configured to receive the caustic outlet stream and output the caustic outlet stream into a metal salt inlet 104d of the quench tower 104. In various examples, the caustic outlet stream can comprise a spent caustic stream.

In various examples, the caustic outlet stream may be produced by various suitable processes. For example, the caustic outlet stream can be produced by a cracking process such as ethylene cracking, a refinery process such as mercaptan oxidation, a paper manufacturing process, a soap manufacturing process, a detergent manufacturing process, a food manufacturing process, any other suitable caustic producing process, and combinations thereof. In various examples, a storage vessel can store caustic waste and the storage vessel can comprise a storage vessel outlet (not shown) suitable to output the caustic outlet stream into the metal salt inlet 104d. Accordingly, the method, the system, and the apparatus according to the present disclosure are not limited to ODH processes and the method, the system, and the apparatus according to the present disclosure can be used with other suitable processes.

In various examples, the caustic waste stream and the ODH outlet stream can be separately and/or concomitantly introduced into the quench tower 104.

The quench tower 104 can be configured to contact the caustic outlet stream with the ODH outlet stream. In various examples, the quench tower 104 can be configured to react the caustic outlet stream with the ODH outlet stream to form a derivative salt and in various examples, a carbon-based oxide and/or a sulfide, from the metal salt and the oxygenate. In various examples, the quench tower 104 can react the metal salt with the oxygenate, and in some examples, with water and caustic agent, to form the derivative salt and the carbon-based oxide and/or sulfide. The derivative salt can comprise an acetate, an acrylate, and a malonate. For example, the acetate can comprise at least one of sodium acetate, potassium acetate, and ammonium acetate. The acrylate can comprise at least one of sodium acrylate, potassium acrylate, and ammonium acrylate. The malonate can comprise at least one of sodium malonate, potassium malonate, and ammonium malonate. In various examples, the derivative salt can be water soluble. As an example, the reaction of sodium bicarbonate and the oxygenate to form sodium acetate, carbon dioxide, and water is illustrated by the reaction in Scheme 2.

Scheme 2

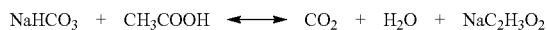

In various examples, the mole ratio of the metal salt in the caustic outlet stream to oxygenate in the ODH outlet stream can be in a range of 0.8:1 to 1.2:1 such as for example, 1:1. In various examples, the mole ratio of the metal salt in the caustic outlet stream to oxygenate in the ODH outlet stream can be greater than 1:1 such as, for example, 2:1.

In various examples, the quench tower 104 can be configured to maintain a pH in a range of 2 to 12 such as, for example, 4 to 11, 4 to 7, or 7 to 11. In various examples, the quench tower 104 can be configured to maintain a pH in a range of a pKa of the oxygenate to a pKa of the metal salt in order to facilitate the formation of the derivative salt. In various examples, the oxygenate comprises acetic acid having a pKa of 4.7 and sodium bicarbonate having a pKa of 10.3. In various examples, the pH is measured in a mixture of water, oxygenate, and metal salt.

The quench outlet stream can comprise a substantial portion of the carbon-based oxide in the quench tower 104 from the ODH outlet stream. In various examples, the carbon-based oxide from ODH outlet stream can pass through the quench tower 104 substantially unreacted. The oxygenate outlet stream can comprise the oxygenate, the derivative salt, and water. Adding the caustic outlet stream to the quench tower can decrease the amount of oxygenate and increase the amount of derivative salt in the quench outlet stream. The decrease in oxygenate in the quench outlet stream can be a result of the conversion of the oxygenate to the derivative salt. The conversion of the oxygenate to the derivative salt can facilitate the removal of the oxygenate from the ODH outlet stream and limit the oxygenate from exiting the quench tower 104 in the alkene outlet stream.

Figure 2:
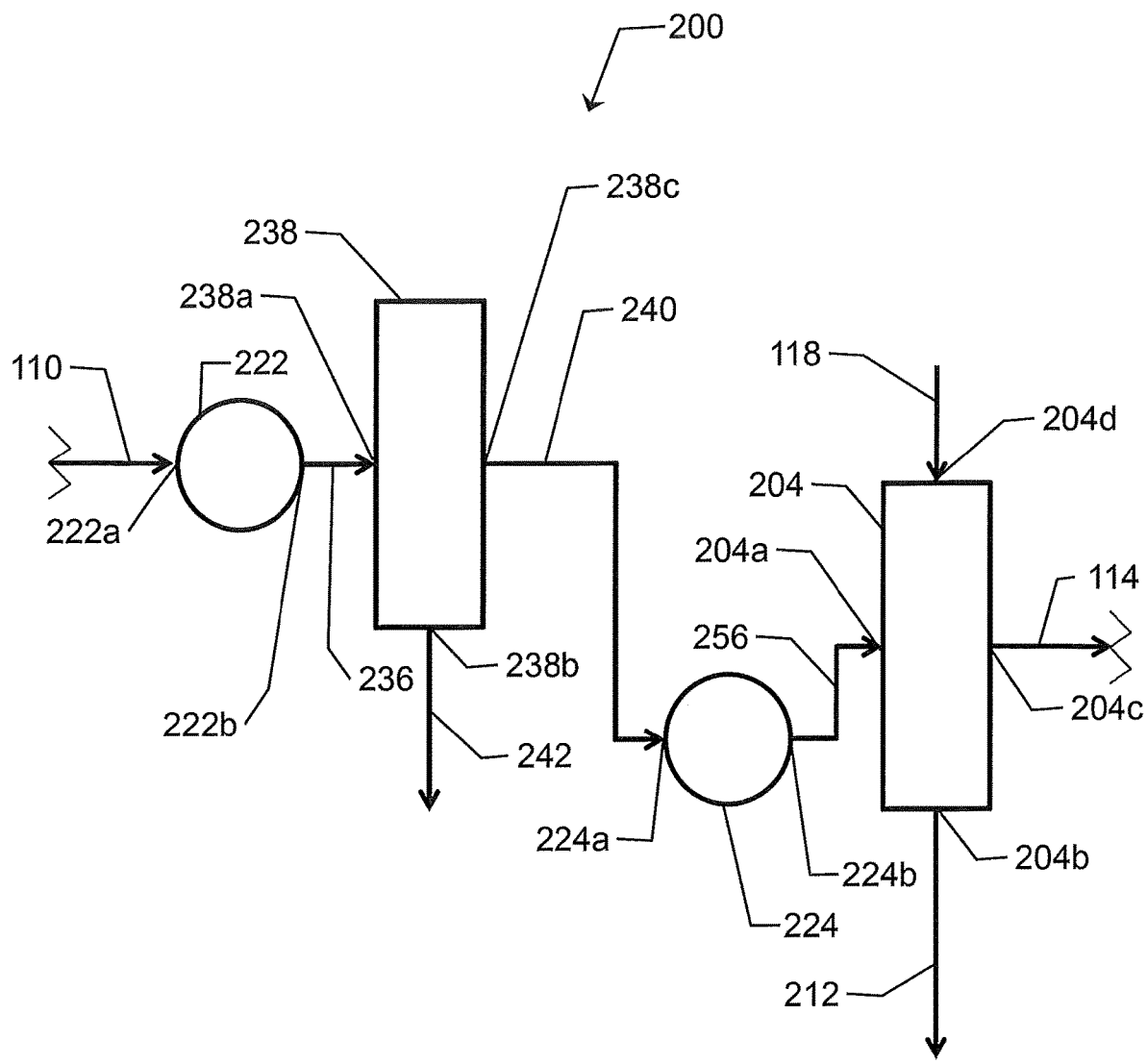
FIG. 2 is a flow diagram illustrating a non-limiting example of a system to separate an oxygenate from a stream including a quench tower with a primary stage and a secondary stage.

The quench tower 104 can be a single stage or multiple stages. For example, referring to FIG. 2, illustrated is a flow diagram of a non-limiting example of a system 200 comprising a multistage quench tower. As illustrated, the ODH outlet line 110 can be in fluid communication with a first heat exchanger (HX) inlet 222a of a first HX 222. The first HX inlet 222a can be configured to receive the ODH outlet stream from the ODH outlet line 110 and can be suitable to transport the ODH outlet stream into the first HX 222. The first HX 222 can be configured to adjust the temperature of the ODH outlet stream. For example, the first HX 222 can cool the ODH outlet stream to a temperature of less than 200° C. such as, for example, less than 100° C., less than 50° C., less than 40° C., and in some examples, the first HX 222 can cool the ODH outlet stream to a temperature of 20° C. to 80° C. In various examples, the first HX 222 can cool the ODH outlet stream to a temperature which induces condensation of the oxygenate such as, for example, a temperature less than or equal to the boiling point of the oxygenate and/or a temperature that reduces the vapor pressure of the oxygenate. The first HX 222 can be any HX as known in the art. For example, the first HX 222 can be a standalone HX separate from a quench tower. In various examples, the first HX 222 can be an integrated HX that is part of a quench tower.

The temperature adjusted ODH outlet stream can exit the first HX 222 through a first HX outlet 222b as a first HX outlet stream. The first HX outlet 222b can be configured to receive the first HX outlet stream and can be suitable to transport the first HX outlet stream out of the first HX 222 into the first HX outlet line 236.

The first HX outlet 222b can be in fluid communication with a separator inlet 238a of a separator 238 via the first HX outlet line 236 to direct the first HX outlet stream to the separator 238. The separator 238 can comprise a vapor-liquid separator such as, for example, a flash drum. The separator inlet 238a can be configured to receive the first HX outlet stream from the first HX outlet line 236 and can be suitable to transport the first HX outlet stream into the separator 238.

The separator 238 can be configured to condense the oxygenate and produce a condensate outlet stream substantially comprised of liquid and an alkene outlet stream substantially comprised of gas. The condensate outlet stream can comprise oxygenate from the first HX outlet stream. In various examples, the condensate outlet stream can comprise at least 80% oxygenate by weight such as, for example, at least 90% oxygenate by weight, at least 95% oxygenate by weight, or 80% to 100% oxygenate by weight. In various examples, the condensate outlet stream can additionally comprise water from the first HX outlet stream.

A condensate outlet 238b of the separator 238 can be configured to receive the condensate outlet stream and can be suitable to transport the condensate outlet stream out of the separator 238 and into the condensate line 242. An alkene outlet 238c of the separator 238 can be configured to receive the alkene outlet stream and can be suitable to transport the alkene outlet stream out of the separator 238 into the alkene outlet line 240.

In various examples, a second HX 224 can be provided in fluid communication with the separator 238. For example, the alkene outlet line 240 can be in fluid communication with a second HX inlet 224a of the second HX 224. The second HX inlet 224a can be configured to receive the alkene outlet stream from the alkene outlet line 240 and can be suitable to transport the ODH outlet stream into the second HX 224. The second HX 224 can be configured to adjust the temperature of the alkene outlet stream. For example, the second HX 224 can cool the alkene outlet stream to a temperature of less than 170° C. such as, for example, less than 100° C., less than 50° C., less than 40° C., and in some examples, the second HX 224 can cool the alkene outlet stream to a temperature of 20° C. to 80° C. In various examples, the second HX 224 can cool the ODH outlet stream to a temperature which induces condensation of the oxygenate such as, for example, a temperature less than or equal to the boiling point of the oxygenate and/or a temperature that reduces the vapor pressure of the oxygenate. The second HX 224 can be any HX as known in the art. For example, the second HX 224 can be a standalone HX separate from a quench tower. In various examples, the second HX 224 can be an integrated HX that is part of a quench tower.

The temperature adjusted ODH outlet stream can exit the second HX 224 through a second HX outlet 224b as a second HX outlet stream. The second HX outlet 224b can be configured to receive the second HX outlet stream and can be suitable to transport the second HX outlet stream out of the second HX 224 into the second HX outlet line 256.

The second HX outlet 224b can be in fluid communication with a quench inlet 204a of a quench tower 204 via the second HX outlet line 256 to direct the second HX outlet stream to the quench tower 204. The quench inlet 204a can be configured to receive the second HX outlet stream from the second HX outlet line 256 and can be suitable to transport the second HX outlet stream into the quench tower 204.

A metal salt inlet 204d of the quench tower 204 can be configured to receive the caustic outlet stream from the return line 118 and can be suitable to transport the caustic outlet stream into the quench tower 204. The quench tower 204 can be configured to contact the caustic outlet stream with the second HX outlet stream. In various examples, the quench tower 204 can be configured to react the caustic outlet stream with the second HX outlet stream to form a derivative salt and in various examples, a carbon-based oxide and/or sulfide. In various examples, the quench tower 204 can react the metal salt with the oxygenate, and in some examples, with water and caustic agent, to form the derivative salt and carbon-based oxide and/or sulfide. The caustic outlet stream can enable more efficient removal of the oxygenate from the alkene outlet stream. Removing more oxygenate from the alkene outlet stream can lengthen the operational life of downstream equipment that can be fouled by formation of a derivative salt from the oxygenate.

The quench tower 204 can be configured to quench the components in the second HX outlet stream and remove at least a substantial portion of the alkene from the second HX outlet stream. In various examples, the quench tower 204 can facilitate the removal of oxygenate and water from the second HX outlet stream. The quench tower 204 can produce a quench outlet stream comprising at least a substantial portion of the alkene and at least a substantial portion of the carbon-based oxide from the second HX outlet stream. In various examples, the quench outlet stream can comprise additional components from the second HX outlet stream such as for example, oxygen, oxygenate, inert diluent, water (e.g., steam), and unreacted alkane. The quench outlet stream exits the quench tower 204 through the quench outlet 204c. The quench outlet 204c can be configured to receive the quench outlet stream and can be suitable to transport the quench outlet stream out of the quench tower 204 into the quench outlet line 114.

The quench tower 204 can produce a derivative salt outlet stream comprising at least a substantial portion of the oxygenate from the second HX outlet stream and/or at least a substantial portion of the derivative salt formed by the quench tower 204. In various examples, the derivative salt outlet stream can comprise additional components from the second HX outlet stream such as, for example, a substantial portion of the water, lower alkane, alkene, oxygen, and carbon-based oxide. The derivative salt outlet stream exits the quench tower 204 through an oxygenate outlet 204b of the quench tower 204. The oxygenate outlet 204b can be configured to receive the derivative salt outlet stream and can be suitable to transport the derivative salt outlet stream out of the quench tower 204 into the oxygenate outlet line 212.

Figure 3:
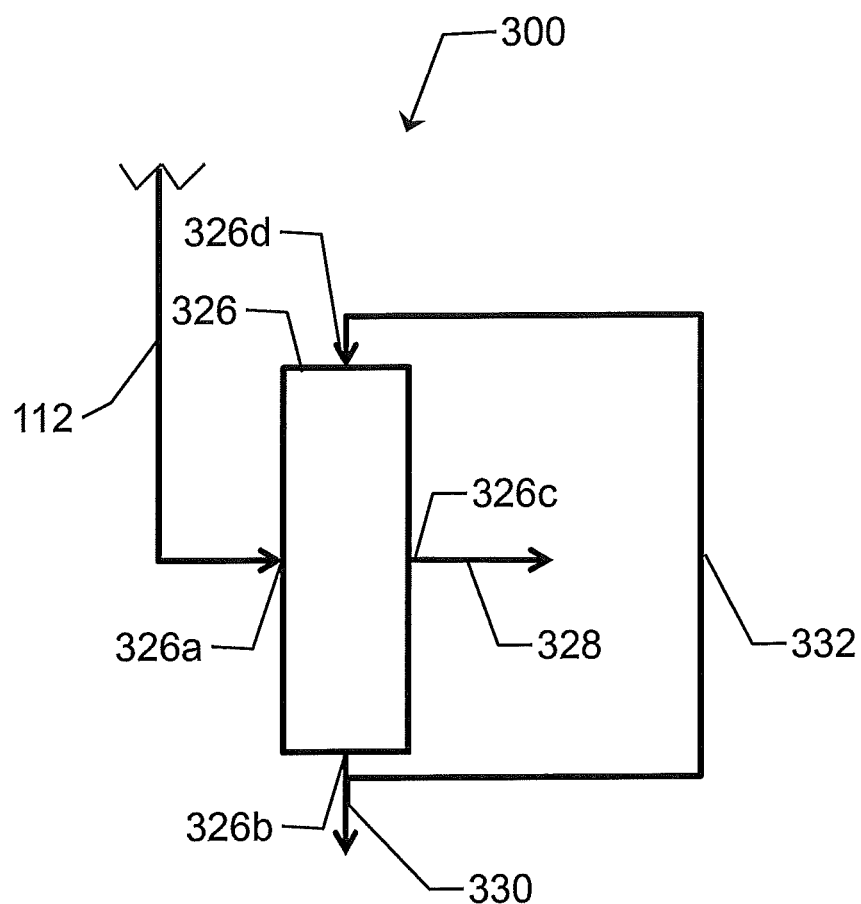
FIG. 3 is a flow diagram illustrating a non-limiting example of a system comprising a separation vessel.

In various examples, the oxygenate in the oxygenate outlet stream, the condensate outlet stream, or derivative salt outlet stream may be subject to further processing. For example, referring to FIG. 3, the oxygenate can be separated from the derivative salt in a separation vessel 326. FIG. 3 is a flow diagram of a non-limiting example of a system 300 comprising the separation vessel 326. As illustrated, the separation vessel 326 has a separation inlet 326a, a first separation outlet 326b, and a second separation outlet 326c. The separation inlet 326a can be configured to receive the oxygenate outlet stream from oxygenate outlet line 112 and may be suitable to transport the oxygenate outlet stream into the separation vessel 326. In various examples, the separation inlet 326a can be configured to receive at least one of the derivative salt outlet stream from the oxygenate outlet line 212 and the condensate outlet stream from the condensate line 242 and may be suitable to transport the respective stream(s) into the separation vessel 326.

The separation vessel 326 can separate the oxygenate from the derivative salt and, in various examples, the separation vessel 326 can separate the oxygenate from water. The presence of the derivative salt in the separation vessel 326 can enhance the separation of oxygenate from the water. For example, the derivative salt and oxygenate may disassociate and/or react with water to form a derivative salt ion (e.g., $CH_3COO^-$) and an acid (e.g., $H_3O^+$, $Na^+$). Since the derivative salt and oxygenate can form a common ion, an increase in the concentration of one of the derivative salt and oxygenate can affect the other. For example, the reactions of sodium acetate ($C_2H_3NaO_2$), acetic acid ($CH_3COOH$), bicarbonate ion ($HCO_3^-$), carbon dioxide ($CO_2$), and water ($H_2O$) is illustrated in Scheme 3.

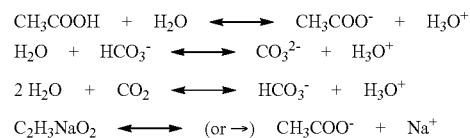

Scheme 3

As illustrated in Scheme 3, sodium acetate can form an acetate ion which can affect the equilibrium reaction of acetic acid and water. For example, the sodium acetate can cause the equilibrium reaction of acetic acid and water to have a higher preference for the separate species of acetic acid and water than an acetate ion and an acid relative to without the presence of acetate.

The separation vessel 326 can comprise various equipment known to those of ordinary skill in the art. For example, the separation vessel 326 can comprise an extraction tower, a packed column, a sieve-tray column, a spray column, a KARR column, a rotating disc contactor, a stirred cell extractor, a rectification tower, a stripper, and combinations thereof. In various examples, the separation vessel 326 can comprise a liquid-liquid extractor. Accordingly, the derivative salt in the oxygenate inlet stream can increase the efficiency of the separation vessel 326 and can facilitate efficient separation of the oxygenate from water.

The separation vessel 326 can produce a second separation outlet stream comprising a substantial portion of the oxygenate from the oxygenate outlet stream. In various examples, the second separation outlet stream can comprise additional components from the oxygenate outlet stream, such as, for example, water. In various examples, the second separation outlet stream can comprise at least 80% oxygenate by weight such as, for example, at least 90% oxygenate by weight, at least 95% oxygenate by weight, or 80% to 100% oxygenate by weight. The second separation outlet stream can exit the separation vessel 326 through the second separation outlet 326c of the separation vessel 326. The second separation outlet 326c can be configured to receive the second separation outlet stream and can be suitable to transport the second separation outlet stream out of the separation vessel 326 into the second separation outlet line 328.

The separation vessel 326 can produce a first separation outlet stream comprising a substantial portion of the derivative salt from the oxygenate outlet stream and in various examples, a substantial portion of the water from the oxygenate outlet stream. In various examples, the first separation outlet stream can comprise at least 10% derivative salt by weight such as, for example, at least 30% derivative salt by weight, at least 50% derivative salt by weight, or 30% to 70% derivative salt by weight. In various examples, the first separation outlet stream can comprise at least 5% water by weight such as, for example, at least 10% water by weight, at least 25% water by weight, or 15% to 50% water by weight. The first separation outlet stream can exit the separation vessel 326 through the first separation outlet 326b of the separation vessel 326. The first separation outlet 326b can be configured to receive the first separation outlet stream and can be suitable to transport the first separation outlet stream out of the separation vessel 326 into the first separation outlet line 330.

The separation vessel 326 can be configured with a recycle line 332 in fluid communication with the first separation outlet line 330 and/or first separation outlet 326b. The recycle line 332 can be configured to recycle a portion of the derivative salt from the first separation outlet stream to the separation vessel 326 via the recycle inlet 326d. The recycle line 332 can be configured to receive a portion of the first separation outlet stream and can be suitable to transport a recycle stream to a recycle inlet 326d of the separation vessel 326. The recycle inlet 326d can be configured to receive the recycle stream and can be suitable to transport the recycle stream into the separation vessel 326. For example, the recycle stream can comprise a portion of the derivative salt from the first separation outlet stream, and in various examples, a portion of the water from the first separation outlet stream.

The recycle line 332 can be configured to recycle the derivative salt from the first separation vessel outlet stream until a select concentration of derivative salt is achieved in the separation vessel 326. In various examples and referring to FIGS. 1 and 3, the return line 118 can enable additional generation of derivative salt in the quench tower 104 which would flow to the separation vessel 326 through the oxygenate outlet line 112 to increase the concentration of derivative salt in the separation vessel 326.

In various examples, a supplemental salt stream can be added to the separation vessel 326. In various examples, the supplemental salt can comprise ethyl acetate.

Figure 4:
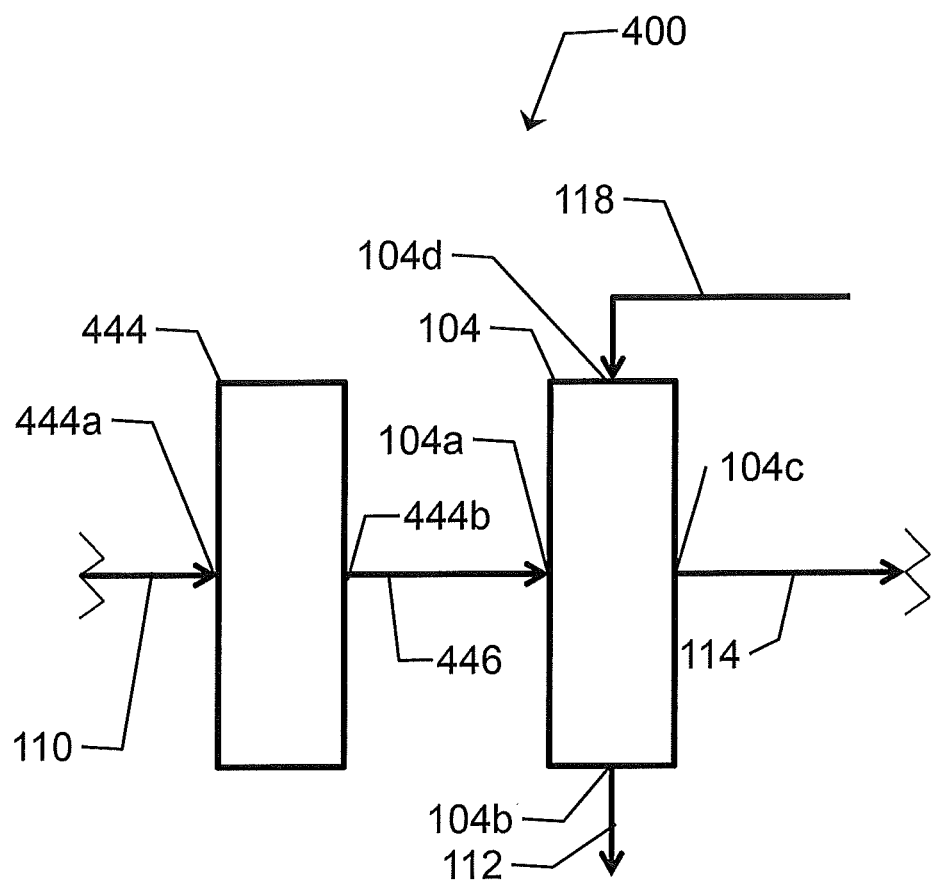
FIG. 4 is a flow diagram illustrating a non-limiting example of a system comprising an oxygen remover.

Referring to FIG. 4, in various examples, an oxygen remover 444 can be disposed intermediate the ODH reactor 102 and the quench tower 104. FIG. 4 is a flow diagram of a non-limiting embodiment of a system 400 comprising an oxygen remover 444. As illustrated, the oxygen remover 444, comprising a remover inlet 444a and a remover outlet 444b, can be provided in fluid communication with the ODH reactor 102 (FIG. 1) via ODH outlet line 110 and the quench tower 104 via remover outlet line 446. The remover inlet 444a can be configured to receive the ODH outlet stream and can be suitable to transport the ODH outlet stream into the oxygen remover 444. The oxygen remover 444 can remove a substantial portion of the oxygen in the ODH outlet stream and produce a remover outlet stream comprising the ODH outlet stream with the substantial portion of the oxygen removed. The oxygen remover 444 can be of various designs as known in the art. The remover outlet 444b can be configured to receive the remover outlet stream and can be suitable to transport the remover outlet stream out of the oxygen remover 444 into the remover outlet line 446. The quench inlet 104a of the quench tower 104 can be configured to receive the remover outlet stream.

Figure 5:
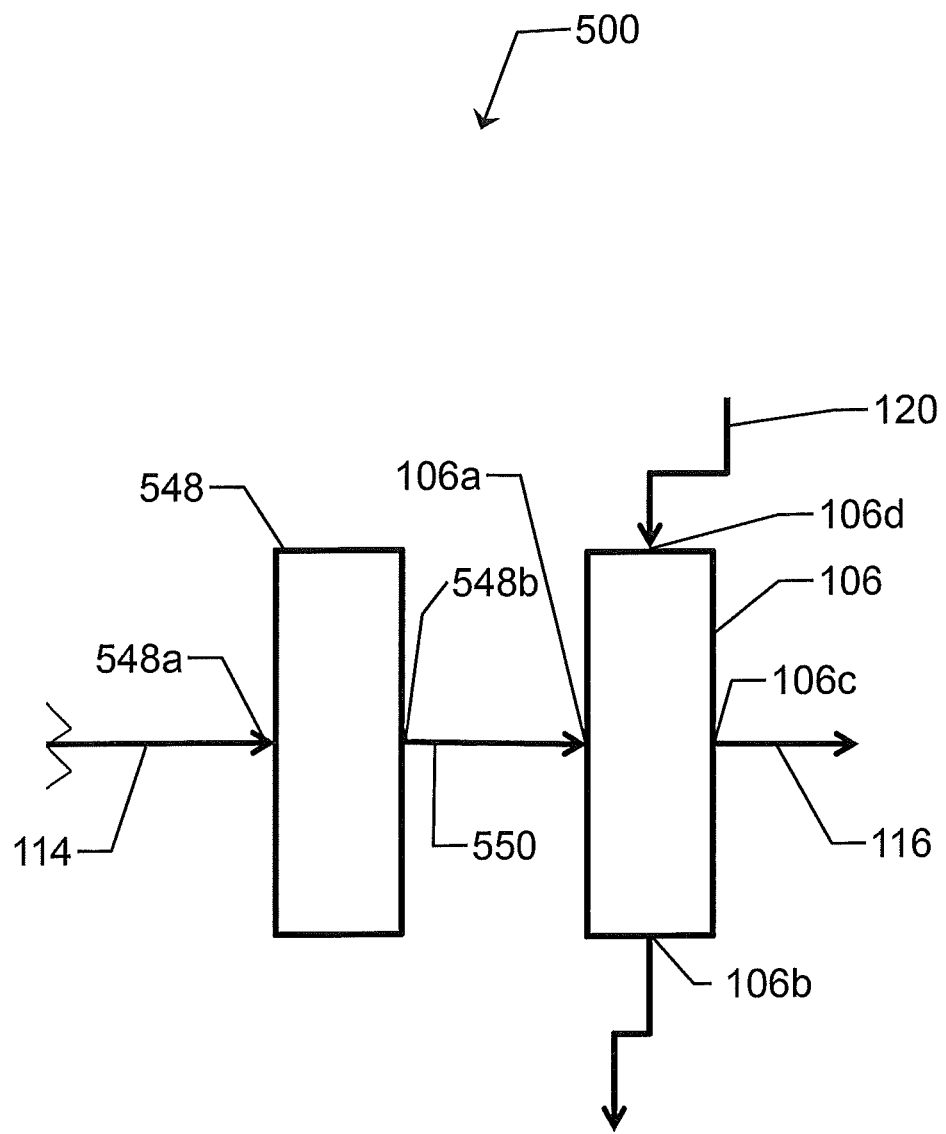
FIG. 5 is a flow diagram illustrating a non-limiting example of a system comprising an amine tower.

Referring to FIG. 5, in various examples, an amine tower 548 can be disposed intermediate the quench tower 104 and the caustic wash tower 106. FIG. 5 is a flow diagram of a non-limiting example of a system 500 comprising an amine tower 548. As illustrated, the amine tower 548, comprising an amine tower inlet 548a and an amine tower outlet 548b, can be provided in fluid communication with the quench tower 104 (FIG. 1) via quench outlet line 114 and the caustic wash tower 106 via amine tower outlet line 550. The amine tower inlet 548a can be configured to receive the quench outlet stream and can be suitable to transport the quench outlet stream into the amine tower 548. The amine tower 548 can remove a substantial portion of carbon dioxide in the quench outlet stream and produce an amine tower outlet stream comprising the quench outlet stream with the substantial portion of the carbon dioxide removed. The amine tower 548 can be of various designs as known in the art.

The amine tower outlet 548b can be configured to receive the amine tower outlet stream and can be suitable to transport the amine tower outlet stream out of the amine tower 548 into the amine tower outlet line 550. The wash inlet 106a of the caustic wash tower 106 can be configured to receive the amine tower outlet stream from the amine tower outlet line 550.

Having a high efficiency oxygenate removal prior to the amine tower 548 can limit, and in some examples prevent, amine degradation to presence of the oxygenate in the amine tower 548. For example, the oxygenate can form heat stable salts with amine in the amine tower 548 which can degrade the efficiency and shorten the operational life of the amine tower 548.

Figure 6:
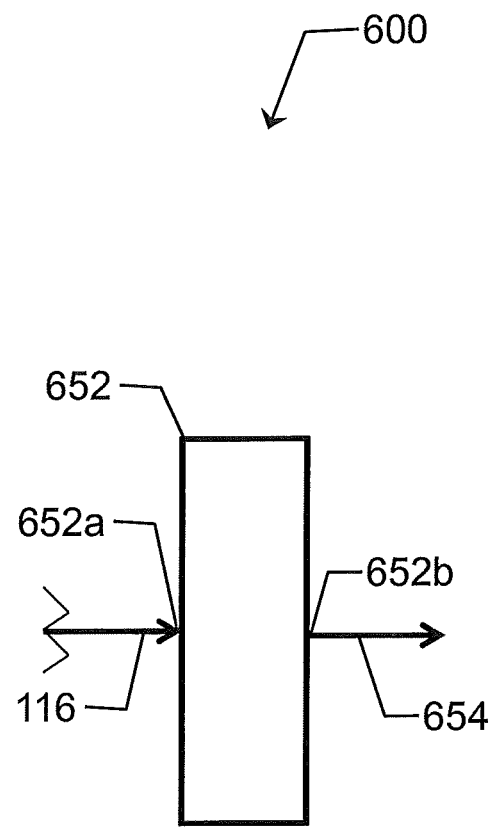
FIG. 6 is a flow diagram illustrating a non-limiting example of a system comprising a polymerization reactor.

Referring to FIG. 6, in various examples, a polymerization reactor 652 can be in fluid communication with the caustic wash tower 106 via the wash outlet line 116. FIG. 6 is a flow diagram of a non-limiting example of a system 600 comprising a polymerization reactor 652. As illustrated, the polymerization reactor 652, comprising a polymerization inlet 652a and a polymerization outlet 652b, can be provided in fluid communication with the caustic wash tower 106 via the wash outlet line 116. In various examples, a demethanizer (not shown) may be disposed in the wash outlet line 116 between the caustic wash tower 106 and the polymerization reactor 652. The polymerization inlet 652a can be configured to receive the ODH outlet stream and can be suitable to transport the ODH outlet stream into the polymerization reactor 652. The polymerization reactor 652 can produce a polymer from the alkene and produce a polymerization outlet stream comprising the polymer. In various examples, the polymer comprises at least one of polyethylene, polypropylene, and polybutylene. The polymerization reactor 652 can be of various designs as known in the art. The polymerization outlet 652b can be configured to receive the polymerization outlet stream and can be suitable to transport the polymerization outlet stream out of the polymerization reactor 652 into the polymerization outlet line 654.

Concentrations of the components within the system can be measured any at point in the process using any means known in the art. For example, a detector such as a gas chromatograph, an infrared spectrometer, and a Raman spectrometer can be disposed downstream or upstream of ODH reactor 102, quench tower 104, caustic wash tower 106, separator 238, separation vessel 326, oxygen remover 444, amine tower 548, and polymerization reactor 652.

In various examples, the ODH inlet stream 108 can comprise mixtures that fall within the flammability limits of the components. For example, the mixture may exist in conditions that prevent propagation of an explosive event. In these examples, the flammable mixture can be created within a medium where ignition can be immediately quenched. In various examples, oxygen and the lower alkanes can be mixed at a point where they are surrounded by a flame arresting material. Thus, any ignition can be quenched by the surrounding material. Flame arresting material includes, for example, metallic or ceramic components, such as stainless steel walls or ceramic supports. In various examples, oxygen and lower alkanes can be mixed at a low temperature, where an ignition event may not lead to an explosion, then the mixture can be introduced into the ODH reactor before increasing the temperature. Therefore, the flammable conditions may not exist until the mixture can be surrounded by the flame arresting material inside of the reactor.

In various examples, the olefins produced using an ODH reactor, or any of the processes or complexes described herein, can be used to make various olefin derivatives utilizing a polymerization reactor. Olefin derivatives include, but are not limited to, polyethylene, polypropylene, ethylene oxide, propylene oxide, polyethylene oxide, polypropylene oxide, vinyl acetate, vinyl chloride, acrylic esters (e.g., methyl methacrylate), thermoplastic elastomers, thermoplastic olefins, blends thereof, and combinations thereof.

In various examples, ethylene and optionally α-olefins can be produced in an ODH reactor, or any of the processes or complexes described herein, and are used to make polyethylene utilizing a polymerization reactor. The polyethylene made from the ethylene and optional α-olefins described herein can include homopolymers of ethylene, copolymers of ethylene and α-olefins, resulting in HDPE, MDPE, LDPE, LLDPE and VLDPE.

The polyethylene produced using the ethylene and optional α-olefins described herein can be produced using any suitable polymerization process and equipment. Suitable ethylene polymerization processes include, but are not limited to gas phase polyethylene processes, high pressure polyethylene processes, low pressure polyethylene processes, solution polyethylene processes, slurry polyethylene processes and suitable combinations of the above arranged either in parallel or in series.

A process for converting a lower alkane to an alkene according to the present disclosure can include introducing an input stream comprising oxygen and the lower alkane to an ODH reactor 102. In various examples, the input stream additionally can include at least one of a carbon-based oxide, steam, and an inert diluent. At least a portion of the lower alkane can be converted to the alkene in the ODH reactor 102. In various examples, the alkane can comprise ethane and the alkene comprises ethylene. In various examples, the alkane can comprise propane and the alkene comprises propylene. In various examples, the alkane comprises butane and the alkene can comprise butylene. An ODH outlet stream comprising the alkene, an oxygenate, and a carbon-based oxide may be produced. In various examples, the ODH outlet stream can comprise at least one of a sulfide, water, an unreacted alkane, oxygen, and an inert diluent.

The ODH outlet stream to can be introduced to a quench tower 104 and the oxygenate can be removed from the ODH outlet stream in the quench tower 104 to produce a quench outlet stream comprising at least a substantial portion of the alkene and at least a substantial portion of the carbon-based oxide. Additionally, the quench tower 104 can produce an oxygenate outlet stream comprising the at least a substantial portion of the oxygenate.

In various examples, the ODH outlet stream can be introduced to an oxygen remover 444 prior to the quench tower 104. Oxygen can be removed from the ODH outlet stream in the oxygen remover 444 and the ODH outlet stream can be introduced to the quench tower 104 after the oxygen remover 444.

The quench outlet stream can be introduced to a caustic wash tower 106. The quench outlet stream can be contacted with a caustic agent to form a caustic outlet stream comprising a metal salt. In various examples, the quench outlet stream is contacted with the caustic agent in the caustic wash tower 106.

In various examples, the quench outlet stream can be introduced to an amine wash tower 548 prior to the caustic wash tower 106. A substantial portion of the carbon-based oxide can be removed from the quench outlet stream. The quench outlet stream with the substantial portion of the carbon-based oxide removed can be introduced to the caustic wash tower 106.

The caustic outlet stream can be introduced the quench tower 104 and the ODH outlet stream can be contacted with the caustic outlet stream to form a derivative salt and in various examples a carbon-based oxide and a sulfide. In various examples, the ODH outlet stream is contacted with the caustic outlet stream in the quench tower 104. The oxygenate outlet stream can comprise a substantial portion of the derivative salt. In various examples, the pH of the quench tower 104 can be maintained in a range of 2 to 12 such as, for example, 4 to 11, 4 to 7, or 7 to 11. In various examples, the pH of the quench tower 104 can be maintained in a range of a pKa of the oxygenate to a pKa of the metal salt.

In various examples, the oxygenate outlet stream can be introduced to a separation vessel 326. The oxygenate can be separated from the derivative salt within the oxygenate outlet stream. A second oxygenate outlet stream comprising a substantial portion of the oxygenate from the oxygenate outlet stream can be produced. A separation outlet stream comprising a substantial portion of the derivative salt from the oxygenate outlet stream can be produced. In various examples, a portion of the separation outlet stream can be recycled to the separation vessel 326. In various examples, a supplemental salt can be introduced to the separation vessel 326 such as, for example, ethyl acetate.

In various examples, the ODH outlet stream can be separated into a first intermediate stream and a second intermediate stream. The first intermediate stream can comprise at least a substantial portion of the oxygenate from the ODH outlet stream. The second intermediate stream can comprise at least a substantial portion of the alkene from the ODH outlet stream. The second intermediate stream can contact the caustic outlet stream to form the derivative salt and in various examples a carbon-based oxide and/or a sulfide.

In various examples, olefin derivatives can be produced from the alkene.

The present disclosure can introduce an alternative use for the caustic waste stream which limits, and in some examples, can eliminate a need to dispose of the caustic waste stream. Additionally, the reuse of the caustic waste stream can introduce a useful product of derivative salt which can aid in oxygenate separation from the quench outlet stream and purification of oxygenate in the separation vessel. The efficient removal of the oxygenate from the quench outlet stream can lengthen the operational life of downstream equipment such as protecting the amine tower against fouling and amine solution degradation. Moreover, the derivative salt can be sold. Furthermore, the efficient purification of the oxygenate can create a marketable product such as, for example, glacial acetic acid.

The method, system, and apparatus according to the present disclosure may comprise other suitable process equipment such as, for example, a compressor and a pump.

EXAMPLES

Computational modeling of a liquid-liquid separation vessel using ASPEN Plus® version 8.6 chemical process simulation software, commercially available from Aspen Technology, Inc. Bedford, Mass., was used to demonstrate the increase in concentration of a dilute oxygenate stream using the method described. The model simulates the effect of temperature, mass flow rate and composition of the oxygenate outlet stream on the composition of the separation outlet stream and the second oxygenate outlet stream. The compositions chosen for each example reflect compositions that may be present in an oxygenate outlet stream that is produced from a quench tower downstream from an oxidative dehydrogenation of ethane process. Oxygenate outlet streams from an ethane ODH process typically comprises dilute acetic acid where the acetic acid mass fraction ranges from 1 to 5%, but in some instances may reach 25%. The oxygenate outlet stream may also comprise trace levels of carbon oxides, such as carbon dioxide. Addition of a caustic outlet stream comprising a metal salt into the quench tower may have the effect of reducing the mass fraction of acetic acid in the oxygenate outlet stream.

Example 1

For example 1, input levels represent compositions of carbon dioxide, water, acetic acid, and sodium acetate (as a sodium ion and acetate ion) representative of an oxygenate outlet stream coming directly from the quench tower with no additional sodium acetate added (via a recycle line). The total mass flow rate was set at 6980 kg/hr and at a pressure of 185.7 kPa gauge and a temperature of 40° C. The simulation results revealed a mass flow rate of the separation outlet stream of 5436 kg/hr and a mass flow rate of the second separation outlet stream was 1545 kg/hr.

Example 2

For example 2, input levels represent compositions of carbon dioxide, water, acetic acid, and sodium acetate (as a sodium ion and acetate ion) for the oxygenate outlet stream that includes additional sodium acetate (added via a recycle line). The total mass flow rate was set at 55982 kg/hr and at a pressure of 465 kPa gauge and a temperature of 65° C. The simulation results revealed a mass flow rate of the separation outlet stream of 54917 kg/hr and a mass flow rate of the second separation outlet stream was 975 kg/hr.

Example 3

For example 3, input levels represent compositions of carbon dioxide, water, acetic acid, and sodium acetate (as a sodium ion and acetate ion) for the oxygenate outlet stream that includes additional sodium acetate (added via a recycle line). The total mass flow rate was set at 61014 kg/hr and at a pressure of 465 kPa gauge and a temperature of 52° C. The simulation results revealed a mass flow rate of the separation outlet stream of 60537 kg/hr and a mass flow rate of the second separation outlet stream was 477 kg/hr.

TABLE 1

| | | Oxygen Outlet Stream | | | Separation Outlet Stream | | | Second Oxygenate Outlet Stream | | |
| --- | --- | --- | --- | --- | --- | --- | --- | --- | --- | --- |
| | | | | | Example | | | | | |
| | | 1 | 2 | 3 | 1 | 2 | 3 | 1 | 2 | 3 |
| | Temp (° C.) | 40 | 65 | 52 | 40 | 64 | 53 | 40 | 64 | 53 |
| | Mass flow (kg/hr) | 6980 | 55982 | 61014 | 5436 | 54917 | 60537 | 1545 | 975 | 477 |
| Mass Fraction | $CO_2$ | 0.001 | 0.000 | 0.000 | 0.000 | 0.000 | 0.000 | 0.006 | 0.000 | 0.000 |
| | $H_2O$ | 0.235 | 0.162 | 0.2337 | 0.287 | 0.164 | 0.235 | 0.052 | 0.046 | 0.074 |
| | $CH_3OOH$ | 0.219 | 0.024 | 0.026 | 0.013 | 0.024 | 0.019 | 0.942 | 0.954 | 0.925 |
| | $Na^+$ | 0.153 | 0.228 | 0.208 | 0.196 | 0.232 | 0.210 | 0.000 | 0.000 | 0.000 |
| | $CH_3COO^-$ | 0.392 | 0.586 | 0.533 | 0.504 | 0.596 | 0.537 | 0.000 | 0.000 | 0.000 |

As shown in Table 1, all examples show a significant separation of sodium acetate from acetic acid, resulting in a much more concentrated and purer solution of acetic acid. The second oxygenate outlet stream in each example shows no detectable sodium acetate. Addition of excess sodium acetate to the oxygenate outlet stream via recycling of the separation outlet stream increased mass flow rate without increasing the mass fraction of acetic acid in the second oxygenate outlet stream. However, in both example 2 and 3 the mass fraction of acetic acid in the oxygen outlet stream was significantly lower compared to example 1. This demonstrates that recycling of the separation outlet stream would be helpful for oxygenate outlet streams where oxygenate levels are lower, such as in instances where the quench tower comprises a first stage and a second stage. Removal of a substantial portion of the acetic acid in the first stage results in the stream going to the second stage having a significantly lower mass fraction of acetic acid. These results show that even in this instance the acetic acid level of the second oxygenate outlet stream is over 90% (mass fraction).

ADDITIONAL EMBODIMENTS

The present invention provides for the following exemplary embodiments, the numbering of which is not to be construed as designating levels of importance.

Embodiment 1 provides a method for separation of an oxygenate from a stream, the method including introducing the stream including the oxygenate and a caustic outlet stream including a metal salt to a quench tower, contacting the oxygenate with the metal salt in the quench tower to convert a portion of the oxygenate to a derivative salt, and removing from the quench tower a quench outlet stream and an oxygenate outlet stream including at least a substantial portion of the unconverted oxygenate and at least a substantial portion of the derivative salt.

Embodiment 2 provides the method of embodiment 1, wherein the stream and the caustic outlet stream are introduced separately to the quench tower.

Embodiment 3 provides the method of any of embodiments 1-2, wherein introducing the stream to the quench tower occurs concomitantly with introducing the caustic outlet stream to the quench tower.

Embodiment 4 provides the method of any of embodiments 1-3, wherein the oxygenate outlet stream is introduced to a separation vessel to separate the unconverted oxygenate from the derivative salt, producing a second oxygenate outlet stream including a substantial portion of the unconverted oxygenate from the oxygenate outlet stream and a separation outlet stream including a substantial portion of the derivative salt from the oxygenate outlet stream.

Embodiment 5 provides the method of embodiment 4 wherein a portion of the separation outlet stream is recycled back to the separation vessel.

Embodiment 6 provides the method of any of embodiments 4-5, wherein ethyl acetate is introduced to the separation vessel.

Embodiment 7 provides the method of any of embodiments 1-6, wherein the stream includes at least one of a carbon-based oxide, a sulfide, an unreacted alkane, an alkene, and oxygen and the quench outlet stream includes at least a substantial portion of the at least one of a carbon-based oxide, a sulfide, an unreacted alkane, an alkene, and oxygen that are present in the stream.

Embodiment 8 provides the method of any of embodiments 1-7, wherein the stream includes a carbon-based oxide selected from at least one of carbon monoxide and carbon dioxide.

Embodiment 9 provides the method of any of embodiments 7-8, wherein the carbon-based oxide includes carbon dioxide and further includes introducing the quench outlet stream to an amine wash tower and removing a substantial portion of the carbon-based oxide from the quench outlet stream.

Embodiment 10 provides the method of any of embodiments 1-9, wherein the stream is introduced to an oxygen remover, and oxygen is removed from the stream, if present, prior to introducing the stream to the quench tower.

Embodiment 11 provides the method of any of embodiments 1-10, wherein the pH of the quench tower is maintained in a range of a pKa of the oxygenate to a pKa of the metal salt.

Embodiment 12 provides the method of any of embodiments 1-11, wherein the oxygenate includes acetic acid having a pKa of 4.7 and the metal salt includes sodium bicarbonate having a pKa of 10.3.

Embodiment 13 provides the method of any of embodiments 1-12, wherein a substantial portion of the oxygenate is removed from the stream prior to introducing the stream to the quench tower.

Embodiment 14 provides the method of any of embodiments 1-13, wherein the quench outlet stream is introduced into a caustic wash tower and contacted with a caustic agent selected from least one of sodium hydroxide, potassium hydroxide, and ammonium hydroxide, to form the metal salt which is removed from the caustic wash tower.

Embodiment 15 provides the method of embodiment 14 wherein the metal salt removed from the caustic wash tower is recycled back to the quench tower as a component of the caustic outlet stream.

Embodiment 16 provides the method of any of embodiments 1-15, wherein the metal salt includes at least one of sodium hydrogen sulfide, sodium bicarbonate, potassium carbonate, and ammonium bicarbonate.

Embodiment 17 provides the method of any of embodiments 1-16, wherein the oxygenate includes at least one of acetic acid, acrylic acid, maleic acid, and maleic anhydride.

Embodiment 18 provides the method of any of embodiments 1-17, wherein the derivative salt includes at least one of sodium acetate, potassium acetate, ammonium acetate, sodium acrylate, potassium acrylate, ammonium acrylate, sodium malonate, potassium malonate, and ammonium malonate.

Embodiment 19 provides the method of any of embodiments 1-18, wherein the caustic outlet stream is produced by at least one process selected from an oxidative dehydrogenation process, a cracking process, a refinery process, a paper manufacturing process, a soap manufacturing process, a detergent manufacturing process, and a food manufacturing processing.

Embodiment 20 provides the method of any of embodiments 1-19, wherein the stream includes an alkene including at least one of ethylene and propylene.

Embodiment 21 provides the method of embodiment 20, wherein olefin derivatives are produced from the alkene.

Embodiment 22 provides the method of embodiment 21, wherein the olefin derivatives include at least one of polyethylene, polypropylene, ethylene oxide, propylene oxide, polyethylene oxide, polypropylene oxide, thermoplastic elastomers, and thermoplastic olefins.

Embodiment 23 provides the method of embodiment 22, wherein the olefin derivative is a polyethylene and includes at least one of homopolymers of ethylene, copolymers of ethylene and α-olefins, high density polyethylene (HDPE), medium density polyethylene (MDPE), low density polyethylene (LDPE), linear low density polyethylene (LLDPE), and very low density polyethylene (VLDPE).

Embodiment 24 provides an apparatus for separation of an oxygenate from a stream, the apparatus including a quench tower including a quench inlet for receiving the stream including the oxygenate, a quench outlet for removing a quench outlet stream, a metal salt inlet for introducing a caustic outlet stream including a metal salt, and an oxygenate outlet for removing an oxygenate outlet stream and wherein oxygenate may contact the metal salt in the quench tower to convert a portion of the oxygenate into a derivative salt, a substantial portion of which is removed along with a substantial portion of unconverted oxygenate as a component of the oxygenate outlet stream.

Embodiment 25 provides the apparatus of embodiment 23, further including a separation vessel including a separation inlet in fluid communication with the oxygenate outlet and configured to receive the oxygenate outlet stream, a derivative salt outlet for removing a derivative salt outlet stream including a derivative salt, and a separation outlet configured for removing a separation outlet stream including a substantial portion of the unconverted oxygenate present in the oxygenate outlet stream.

Embodiment 26 provides the apparatus of embodiment 25, wherein the separation vessel further includes a recycle line in fluid communication with the derivative salt outlet to receive the derivative salt outlet stream and direct at least a portion of the derivative salt outlet stream into the separation inlet of the separation vessel.

Embodiment 27 provides the apparatus of any of embodiments 25-26, wherein the separation vessel further includes a supplemental salt inlet suitable for introducing ethyl acetate into the separation vessel.

Embodiment 28 provides the apparatus of any of embodiments 24-27, wherein the stream includes at least one of a carbon-based oxide, a sulfide, water, an unreacted alkane, an alkene, and oxygen.

Embodiment 29 provides the apparatus of embodiment 28, wherein the carbon-based oxide includes at least one of carbon monoxide and carbon dioxide.

Embodiment 30 provides the apparatus of embodiment 29, wherein the carbon-based oxide includes carbon dioxide and further includes an amine wash tower including an amine inlet and an amine outlet, the amine inlet in fluid communication with the quench outlet to receive the quench outlet stream, and the amine wash tower configured to remove at least a portion of the carbon-based oxide from the quench outlet stream.

Embodiment 31 provides the apparatus of any of embodiments 24-30, further including an oxygen remover including a remover inlet and a remover outlet, the oxygen remover suitable to remove oxygen from the stream, and the remover outlet in fluid communication with the quench inlet of the quench tower to direct the stream into the quench inlet.

Embodiment 32 provides the apparatus of any of embodiments 24-31, wherein the quench tower is configured for a pH in a range of a pKa of the oxygenate to a pKa of the metal salt.

Embodiment 33 provides the apparatus of any of embodiments 24-32, wherein the oxygenate includes acetic acid having a pKa of 4.7 and the metal salt includes sodium bicarbonate having a pKa of 10.3.

Embodiment 34 provides the apparatus of any of embodiments 24-33, wherein the quench tower includes a primary stage and a secondary stage, wherein the primary stage is configured to remove a substantial portion of oxygenate in the stream and includes the quench inlet, a first intermediate outlet, and a second intermediate outlet, the first intermediate outlet is configured for removal of the stream from the primary stage and is in fluid communication with an intermediate inlet of the secondary stage, the second intermediate outlet suitable for removing the substantial portion of oxygenate removed from the stream, and the second stage including the quench outlet, the metal salt inlet, and the oxygenate outlet.

Embodiment 35 provides the apparatus of any of embodiments 24-34, further including a caustic wash tower including a wash inlet, a wash outlet, a caustic inlet, and a caustic outlet, the wash inlet in fluid communication with the quench outlet to receive the quench outlet stream, the caustic outlet configured for removing the caustic outlet stream, the caustic inlet configured for introducing at least one of sodium hydroxide, potassium hydroxide, and ammonium hydroxide into the caustic wash tower and wherein the caustic wash tower further includes a return line in fluid communication with the caustic outlet to receive the caustic outlet stream and output the caustic outlet stream into the metal salt inlet of the quench tower.

Embodiment 36 provides the apparatus of any of embodiments 24-35, wherein the metal salt includes at least one of sodium hydrogen sulfide, sodium bicarbonate, potassium carbonate, and ammonium bicarbonate.

Embodiment 37 provides the apparatus of any of embodiments 24-36, wherein the oxygenate includes at least one of acetic acid, acrylic acid, maleic acid, and maleic anhydride.

Embodiment 38 provides the apparatus of any of embodiments 24-37, wherein the derivative salt includes at least one of sodium acetate, potassium acetate, ammonium acetate, sodium acrylate, potassium acrylate, ammonium acrylate, sodium malonate, potassium malonate, and ammonium malonate.

Embodiment 39 provides the apparatus of any of embodiments 24-38, wherein the caustic outlet stream is produced by at least one process selected from an oxidative dehydrogenation process, a cracking process, a refinery process, a paper manufacturing process, a soap manufacturing process, a detergent manufacturing process, and a food manufacturing processing.

Embodiment 40 provides the apparatus of any of embodiments 24-39, wherein the stream includes an alkene including at least one of ethylene and propylene.

Embodiment 41 provides the apparatus of embodiment 40, further including a polymerization reactor suitable to make olefin derivatives from the alkene.

Embodiment 42 provides the apparatus of embodiment 41, wherein the olefin derivatives include at least one of polyethylene, polypropylene, ethylene oxide, propylene oxide, polyethylene oxide, polypropylene oxide, thermoplastic elastomers, and thermoplastic olefins.

Embodiment 43 provides the apparatus of embodiment 42, wherein the olefin derivative is polyethylene and includes at least one of homopolymers of ethylene, copolymers of ethylene and α-olefins, high density polyethylene (HDPE), medium density polyethylene (MDPE), low density polyethylene (LDPE), linear low density polyethylene (LLDPE), and very low density polyethylene (VLDPE).

Embodiment 44 provides for a system for separation of an oxygenate from a stream, the system including a quench tower configured to receive the stream including the oxygenate and a caustic outlet stream including a metal salt, contact the oxygenate with the metal salt to convert a portion of the oxygenate to a derivative salt, quench the derivative salt and unconverted oxygenate, produce a quench outlet stream including the stream with a substantial portion of the oxygenate removed, and produce an oxygenate outlet stream including at least a substantial portion of the unconverted oxygenate and at least a substantial portion of the derivative salt.

Embodiment 45 provides the system of embodiment 44 further including a separation vessel configured to receive the oxygenate outlet stream, separate the unconverted oxygenate from the derivative salt within the first oxygenate outlet stream, produce a second oxygenate outlet stream including a substantial portion of the unconverted oxygenate from the oxygenate outlet stream, and produce a separation outlet stream including a substantial portion of the derivative salt from the oxygenate outlet stream.

Embodiment 46 provides the system of embodiment 45, wherein the separation vessel further includes a recycle line configured to recycle a portion of the separation outlet stream into the separation vessel.

Embodiment 47 provides the system of any of embodiments 45-46, wherein the separation vessel is further configured to receive ethyl acetate.

Embodiment 48 provides the system of any of embodiments 44-47, wherein the stream includes at least one of a carbon-based oxide, a sulfide, an unreacted alkane, an alkene, and oxygen.

Embodiment 49 provides the system of embodiment 48, wherein the carbon-based oxide includes at least one of carbon monoxide and carbon dioxide.

Embodiment 50 provides the system of embodiment 49, wherein the carbon-based oxide includes carbon dioxide and further includes an amine wash tower configured to receive the quench outlet stream and remove at least a portion of the carbon-based oxide from the quench outlet stream.

Embodiment 51 provides the system of any of embodiments 44-50, further including an oxygen remover configured to remove oxygen from the stream and direct the stream into the quench tower.

Embodiment 52 provides the system of any of embodiments 44-51, wherein the quench tower is configured to maintain a pH in a range of a pKa of the oxygenate to a pKa of the metal salt.

Embodiment 53 provides the system of any of embodiments 44-52, wherein the quench tower is configured to maintain a pH in a range of 2 to 12.

Embodiment 54 provides the system of any of embodiments 44-53 wherein the quench tower includes two stages, the first stage configured to remove a substantial portion of the oxygenate from the stream, and the second stage configured to receive the stream with a substantial portion of the oxygenate removed.

Embodiment 55 provides the system of any of embodiments 44-54, further including a caustic wash tower configured to receive the quench outlet stream and a caustic agent selected from at least one of sodium hydroxide, potassium hydroxide, and ammonium hydroxide, contact a substantial portion of the carbon-based oxide from the quench outlet stream with the caustic agent to form a metal salt, and produce the caustic outlet stream, and includes a return line configured to direct the caustic outlet stream from the caustic wash tower into the quench tower.

Embodiment 56 provides the system of any of embodiments 44-55, wherein the metal salt includes at least one of sodium hydrogen sulfide, sodium bicarbonate, potassium carbonate, and ammonium bicarbonate.

Embodiment 57 provides the system of any of embodiments 44-56, wherein the oxygenate includes at least one of acetic acid, acrylic acid, maleic acid, and maleic anhydride.

Embodiment 58 provides the system of any of embodiments 44-57, wherein the derivative salt includes at least one of sodium acetate, potassium acetate, ammonium acetate, sodium acrylate, potassium acrylate, ammonium acrylate, sodium malonate, potassium malonate, and ammonium malonate.

Embodiment 59 provides the system of any of embodiments 44-58, wherein the caustic outlet stream is produced by at least one process selected from an oxidative dehydrogenation process, a cracking process, a refinery process, a paper manufacturing process, a soap manufacturing process, a detergent manufacturing process, and a food manufacturing processing.

Embodiment 60 provides the system of any of embodiments 44-59, wherein the stream further includes an alkene including at least one of ethylene and propylene.

Embodiment 61 provides the system of embodiment 60, further including a polymerization reactor configured to make olefin derivatives from the alkene.

Embodiment 62 provides the system of embodiment 61, wherein the olefin derivatives include at least one of polyethylene, polypropylene, ethylene oxide, propylene oxide, polyethylene oxide, polypropylene oxide, thermoplastic elastomers, and thermoplastic olefins.

Embodiment 63 provides the system of embodiment 62, wherein olefin derivative is polyethylene and includes at least one of homopolymers of ethylene, copolymers of ethylene and α-olefins, high density polyethylene (HDPE), medium density polyethylene (MDPE), low density polyethylene (LDPE), linear low density polyethylene (LLDPE), and very low density polyethylene (VLDPE).

Embodiment 64 provides a method for converting a lower alkane to an alkene including introducing an input stream including oxygen and the lower alkane to an oxidative dehydrogenation (ODH) reactor and converting at least a portion of the lower alkane to the alkene in the ODH reactor and producing an ODH outlet stream including the alkene, unconverted lower alkane, an oxygenate, and a carbon-based oxide, introducing the ODH outlet stream and a caustic outlet stream including a metal salt to a quench tower, contacting the oxygenate with the metal salt within the quench to convert a portion of the oxygenate to a derivative salt, quenching a substantial portion of the unconverted oxygenate and a substantial portion of the derivative salt, removing a quench outlet stream including the alkene, the unconverted lower alkane, and the carbon-based oxide from the quench tower, and removing an oxygenate outlet stream including the quenched derivative salt and the quenched unconverted oxygenate from the quench tower.

Embodiment 65 provides the method of embodiment 64, further including introducing the quench outlet stream to a caustic wash tower including a caustic agent, contacting the carbon-based oxide from the quench outlet stream with the caustic agent in the caustic wash tower to form a metal salt, removing a caustic outlet stream including the metal salt from the caustic wash tower, and introducing the caustic outlet stream to the quench tower with the ODH outlet stream.

Embodiment 66 provides the method of any of embodiments 64-65, further including introducing the oxygenate outlet stream to a separation vessel and separating the unconverted oxygenate from the derivative salt in the separation vessel to produce a second oxygenate outlet stream including a substantial portion of the unconverted oxygenate from the oxygenate outlet stream and a separation outlet stream including a substantial portion of the derivative salt from the oxygenate outlet stream.

Embodiment 67 provides the method of embodiment 66, further including recycling a portion of the separation outlet stream including the derivative salt to the separation vessel.

Embodiment 68 provides the method of any of embodiments 66-67, further including introducing ethyl acetate to the separation vessel.

Embodiment 69 provides the method of any of embodiments 64-68, wherein the carbon-based oxide includes carbon dioxide and further includes introducing the quench outlet stream to an amine wash tower and removing a substantial portion of the carbon-based oxide from the quench outlet stream prior to introducing the quench outlet stream to the caustic wash tower.

Embodiment 70 provides the method of any of embodiments 64-69, wherein the ODH outlet stream further includes at least one of a sulfide, water, and oxygen.

Embodiment 71 provides the method of any of embodiments 64-70, further including introducing the ODH outlet stream to an oxygen remover and removing oxygen from the ODH outlet stream in the oxygen remover prior to introducing the ODH outlet stream to the quench tower.

Embodiment 72 provides the method of any of embodiments 64-71, further including maintaining a pH of the quench tower in a range of a pKa of the oxygenate to a pKa of the metal salt.

Embodiment 73 provides the method of any of embodiments 64-72, wherein the oxygenate includes acetic acid having a pKa of 4.7 and the metal salt includes sodium bicarbonate having a pKa of 10.3.

Embodiment 74 provides the method of any of embodiment 64-73, further including removing a substantial portion of the oxygenate within the ODH outlet stream prior to introducing the ODH outlet stream into the quench tower.

Embodiment 75 provides the method of any of the embodiments 65-74, wherein the caustic agent includes at least one of sodium hydroxide, potassium hydroxide, and ammonium hydroxide.

Embodiment 76 provides the method of any of embodiments 64-75, wherein the metal salt includes at least one of sodium bicarbonate, potassium carbonate, and ammonium bicarbonate.

Embodiment 77 provides the method of any of embodiments 64-76, wherein the carbon-based oxide includes at least one of carbon monoxide and carbon dioxide.

Embodiment 78 provides the method of any of embodiments 64-77, wherein the oxygenate includes at least one of acetic acid, acrylic acid, maleic acid, and maleic anhydride.

Embodiment 79 provides the method of any of embodiments 64-78, wherein the derivative salt includes at least one of sodium acetate, potassium acetate, ammonium acetate, sodium acrylate, potassium acrylate, ammonium acrylate, sodium malonate, potassium malonate, and ammonium malonate.

Embodiment 80 provides the method of any of embodiment 64-79, wherein the lower alkane includes ethane and the alkene includes ethylene.

Embodiment 81 provides the method of any of embodiments 64-79, wherein the lower alkane includes propane and the alkene includes propylene.

Embodiment 82 provides the method of any of embodiments 64-81, further including producing olefin derivatives from the alkene.

Embodiment 83 provides the method of embodiment 82, wherein the olefin derivatives include at least one of polyethylene, polypropylene, ethylene oxide, propylene oxide, polyethylene oxide, polypropylene oxide, thermoplastic elastomers, and thermoplastic olefins.

Embodiment 84 provides the method of embodiment 83, wherein the olefin derivative includes polyethylene and includes at least one of homopolymers of ethylene, copolymers of ethylene and α-olefins, high density polyethylene (HDPE), medium density polyethylene (MDPE), low density polyethylene (LDPE), linear low density polyethylene (LLDPE), and very low density polyethylene (VLDPE).

Embodiment 85 provides an apparatus for oxidative dehydrogenation (ODH) of a lower alkane to an alkene, the apparatus including an ODH reactor including an ODH inlet and an ODH outlet, the ODH inlet configured to receive an ODH inlet stream including the lower alkane into the ODH reactor, the ODH outlet suitable for removing an ODH outlet stream including the alkene, unconverted lower alkane, an oxygenate, and a carbon-based oxide from the ODH reactor, a quench tower including a quench inlet, a quench outlet, a metal salt inlet, and an oxygenate outlet, the quench inlet in fluid communication with the ODH outlet to receive the ODH outlet stream, the quench outlet configure to remove a quench outlet stream including at least a substantial portion of the alkene and at least a substantial portion of the carbon-based oxide from the quench tower, the metal salt inlet configured to receive a caustic outlet stream including a metal salt, the oxygenate outlet suitable for removing an oxygenate outlet stream including at least a substantial portion of the oxygenate and a derivative salt, a caustic wash tower including a wash inlet, a wash outlet, a caustic inlet, and a caustic outlet, the wash inlet in fluid communication with the quench outlet to receive the quench outlet stream, the caustic outlet suitable for transporting a caustic outlet stream including a metal salt, and a return line in fluid communication with the caustic outlet to receive the caustic outlet stream and output the caustic outlet stream into the metal salt inlet of the quench tower.

Embodiment 86 provides the apparatus of embodiment 85, further including a separation vessel including a separation inlet, a derivative salt outlet, and a separation outlet, the separation inlet in fluid communication with the oxygenate outlet to receive the oxygenate outlet stream, the derivative salt outlet suitable for transporting a separation outlet stream including a derivative salt, the separation outlet suitable for transporting a second oxygenate outlet stream including a substantial portion of the oxygenate.

Embodiment 87 provides the apparatus of embodiment 86, wherein the separation vessel further includes a recycle line in fluid communication with the derivative salt outlet to receive the separation outlet stream and output at least a portion of the separation outlet stream into the separation inlet of the separation vessel.

Embodiment 88 provides the apparatus of embodiment 87, wherein the separation vessel further includes a supplemental salt inlet suitable for introducing ethyl acetate into the separation vessel.

Embodiment 89 provides the apparatus of any of embodiments 85-88, further including an amine wash tower including an amine inlet and an amine outlet, the amine inlet in fluid communication with the quench outlet to receive the quench outlet stream, the amine wash tower suitable to remove at least a portion of the carbon-based oxide from the quench outlet stream, and the amine outlet in fluid communication with the wash inlet of the caustic wash tower to output the quench outlet stream into the wash inlet.

Embodiment 90 provides the apparatus of any of embodiments 85-89, wherein the ODH outlet stream further includes at least one of a sulfide, water, an unreacted alkane, and oxygen.

Embodiment 91 provides the apparatus of any of embodiments 85-90, further including an oxygen remover including a remover inlet and a remover outlet, the remover inlet in fluid communication with the ODH outlet to receive the ODH outlet stream, the oxygen remover suitable to remove oxygen from the ODH outlet stream, and the remover outlet in fluid communication with the quench inlet of the quench tower to output the ODH outlet stream into the quench inlet.

Embodiment 92 provides the apparatus of any of embodiments 85-91, wherein the quench tower is suitable for a pH in a range of a pKa of the oxygenate to a pKa of the metal salt.

Embodiment 93 provides the apparatus of any of embodiments 85-92, wherein the oxygenate includes acetic acid having a pKa of 4.7 and the metal salt includes sodium bicarbonate having a pKa of 10.3.

Embodiment 94 provides the apparatus of any of embodiments 85-93, wherein the quench tower further includes a primary stage and a secondary stage, the primary stage configured to remove a substantial portion of the oxygenate from the ODH outlet stream and includes the quench inlet, a first intermediate outlet, and a second intermediate outlet, the first intermediate outlet in fluid communication with an intermediate inlet of the secondary stage, the second intermediate outlet suitable for removing oxygenate removed from the ODH outlet stream, and the second stage including the quench outlet, the metal salt inlet, and the oxygenate outlet.

Embodiment 95 provides the apparatus of any of embodiments 85-94, wherein the caustic inlet is suitable for transporting at least one of sodium hydroxide, potassium hydroxide, and ammonium hydroxide to the caustic wash tower.

Embodiment 96 provides the apparatus of any of embodiments 85-95, wherein the metal salt includes at least one of sodium bicarbonate, potassium carbonate, and ammonium bicarbonate.

Embodiment 97 provides the apparatus of any of embodiments 85-96, wherein the carbon-based oxide includes at least one of carbon monoxide and carbon dioxide.

Embodiment 98 provides the apparatus of any of embodiments 85-97, wherein the oxygenate includes at least one of acetic acid, acrylic acid, maleic acid, and maleic anhydride.

Embodiment 99 provides the apparatus of any of embodiments 85-99, wherein the derivative salt includes at least one of sodium acetate, potassium acetate, ammonium acetate, sodium acrylate, potassium acrylate, ammonium acrylate, sodium malonate, potassium malonate, and ammonium malonate.

Embodiment 100 provides the apparatus of any of embodiments 85-99, wherein the lower alkane includes ethane and the alkene includes ethylene.

Embodiment 101 provides the apparatus of any of embodiments 85-99, wherein the lower alkane includes propane and the alkene includes propylene.

Embodiment 102 provides the apparatus of any of embodiments 85-101, further including a polymerization reactor suitable to make olefin derivatives from the alkene.

Embodiment 103 provides the apparatus of embodiment 102, wherein the olefin derivatives include at least one of polyethylene, polypropylene, ethylene oxide, propylene oxide, polyethylene oxide, polypropylene oxide, thermoplastic elastomers, and thermoplastic olefins.

Embodiment 104 provides the apparatus of embodiment 103, wherein the olefin derivative includes polyethylene and includes at least one of homopolymers of ethylene, copolymers of ethylene and α-olefins, high density polyethylene (HDPE), medium density polyethylene (MDPE), low density polyethylene (LDPE), linear low density polyethylene (LLDPE), and very low density polyethylene (VLDPE).

Embodiment 105 provides a system for oxidative dehydrogenation (ODH) of a lower alkane, the system including an ODH reactor configured to receive an input stream including oxygen and the lower alkane and to produce an ODH outlet stream including an alkene, an oxygenate, and a carbon-based oxide, a quench tower configured to receive the ODH outlet stream and a caustic outlet stream including a metal salt, contact the oxygenate with the metal salt to convert a portion of the oxygenate to a derivative salt, quench the ODH outlet stream, substantially remove the unconverted oxygenate and the derivative salt from the ODH outlet stream, produce a quench outlet stream including at least a substantial portion of the alkene and at least a substantial portion of the carbon-based oxide, and produce an oxygenate outlet stream including at least a substantial portion of the unconverted oxygenate and at least a substantial portion of the derivative salt, a caustic wash tower configured to receive the quench outlet stream and contact a substantial portion of the carbon-based oxide from the quench outlet stream with a caustic agent to form a caustic outlet stream including a metal salt, and a return line configured to direct the caustic outlet stream into the quench tower and contact the caustic outlet stream with the ODH outlet stream to form the derivative salt from the metal salt and the oxygenate, wherein the oxygenate outlet stream includes a substantial portion of the derivative salt.

Embodiment 106 provides the system of embodiment 105, further including a separation vessel configured to receive the oxygenate outlet stream and separate the oxygenate from the derivative salt within the oxygenate outlet stream to produce a second oxygenate outlet stream including a substantial portion of the oxygenate from the oxygenate outlet stream and a separation outlet stream including a substantial portion of the derivative salt from the first oxygenate stream.

Embodiment 107 provides the system of embodiment 106, wherein the separation vessel further includes a recycle line configured to recycle a portion of the separation outlet stream including the derivative salt to the separation vessel.

Embodiment 108 provides the system of any of embodiments 106-107, wherein the separation vessel is configured to receive ethyl acetate.

Embodiment 109 provides the system of any of embodiments 105-108, further including an amine wash tower configured to receive the quench outlet stream, remove at least a portion of the carbon-based oxide from the quench outlet stream, and output the quench outlet stream into the caustic wash tower.

Embodiment 110 provides the system of any of embodiments 105-109, wherein the ODH outlet stream further includes at least one of a sulfide, water, an unreacted alkane, and oxygen.

Embodiment 111 provides the system of any of embodiments 105-110, further including an oxygen remover configured to remove oxygen from the ODH outlet stream and suitable to output the ODH outlet stream into the quench tower.

Embodiment 112 provides the system of any of embodiments 105-111, wherein the quench tower is configured to maintain a pH in a range of a pKa of the oxygenate to a pKa of the metal salt.

Embodiment 113 provides the system of any of embodiments 105-112, wherein the quench tower is configured to maintain a pH in a range of 2 to 12.

Embodiment 114 provides the system of any of embodiments 105-113, wherein the quench tower includes a primary stage and second stage, the primary stage configured to remove a substantial portion of the oxygenate from the ODH outlet stream before directing the ODH outlet stream to the second stage, the second stage configured to contact the ODH outlet stream with the caustic outlet stream to form a derivative salt from the metal salt and the oxygenate.

Embodiment 115 provides the system of any of embodiments 105-114, wherein the caustic agent includes at least one of sodium hydroxide, potassium hydroxide, and ammonium hydroxide to the caustic wash tower.

Embodiment 116 provides the system of any of embodiments 105-115, wherein the metal salt includes at least one of sodium bicarbonate, potassium carbonate, and ammonium bicarbonate.

Embodiment 117 provides the system of any of embodiments 105-116, wherein the carbon-based oxide includes at least one of carbon monoxide and carbon dioxide.

Embodiment 118 provides the system of any of embodiments 105-117, wherein the oxygenate includes at least one of acetic acid, acrylic acid, maleic acid, and maleic anhydride.

Embodiment 119 provides the system of any of embodiments 105-118, wherein the derivative salt includes at least one of sodium acetate, potassium acetate, ammonium acetate, sodium acrylate, potassium acrylate, ammonium acrylate, sodium malonate, potassium malonate, and ammonium malonate.

Embodiment 120 provides the system of any of embodiments 105-119, wherein the lower alkane includes ethane and the alkene includes ethylene.

Embodiment 121 provides the system of any of embodiments 105-119, wherein the lower alkane includes propane and the alkene includes propylene.

Embodiment 122 provides the system of any of embodiments 105-121, further including a polymerization reactor configured to make olefin derivatives from the alkene.

Embodiment 123 provides the system of embodiment 122, wherein the olefin derivatives include at least one of polyethylene, polypropylene, ethylene oxide, propylene oxide, polyethylene oxide, polypropylene oxide, thermoplastic elastomers, and thermoplastic olefins.

Embodiment 124 provides the system of embodiment 123, wherein the olefin derivative includes polyethylene and includes at least one of homopolymers of ethylene, copolymers of ethylene and α-olefins, high density polyethylene (HDPE), medium density polyethylene (MDPE), low density polyethylene (LDPE), linear low density polyethylene (LLDPE), and very low density polyethylene (VLDPE).

One skilled in the art will recognize that the herein described components, devices, operations/actions, and objects, and the discussion accompanying them are used as examples for the sake of conceptual clarity and that various configuration modifications are contemplated. Consequently, as used herein, the specific examples/embodiments set forth and the accompanying discussion are intended to be representative of their more general classes. In general, use of any specific exemplar is intended to be representative of its class, and the non-inclusion of specific components, devices, operations/actions, and objects should not be taken limiting.

While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

What is claimed is:

1. A method comprising:
   introducing an input stream comprising a lower alkane and oxygen to an oxidative dehydrogenation (ODH) reactor;
   converting the lower alkane to an alkene in the ODH reactor and producing an ODH outlet stream comprising the alkene, unconverted lower alkane, an oxygenate, and a carbon-based oxide, wherein the oxygenate is a co-product of an ODH reaction in the ODH reactor;
   introducing the ODH outlet stream comprising the oxygenate and a caustic outlet stream comprising a metal salt to a quench tower;
   contacting the oxygenate with the metal salt in the quench tower to convert a portion of the oxygenate to a derivative salt comprising at least one of an acetate, an acrylate, or a malonate, wherein the derivative salt is formed from the metal salt and the oxygenate; and
   removing from the quench tower:
      a quench outlet stream; and
      an oxygenate outlet stream comprising at least a substantial portion of the unconverted oxygenate and at least a substantial portion of the derivative salt.

2. The method of claim 1, wherein the caustic outlet stream is produced from a caustic wash tower, wherein the ODH outlet stream and the caustic outlet stream are introduced separately to the quench tower, wherein the lower alkane comprises at least one of ethane or propane, wherein the alkene comprises at least one of ethylene or propylene, and wherein the metal salt comprises a carbonate.

3. The method of claim 2, wherein the caustic wash tower processes the quench outlet stream, wherein introducing the ODH outlet stream to the quench tower occurs concomitantly with introducing the caustic outlet stream to the quench tower, wherein the lower alkane comprises ethane, wherein the alkene comprises ethylene, wherein the carbonate comprises at least one of sodium bicarbonate, potassium carbonate, or ammonium bicarbonate, and wherein the derivative salt comprises the acetate.

4. The method of claim 1 further comprising:
   introducing the oxygenate outlet stream to a separation vessel and separating the unconverted oxygenate from the derivative salt via the separation vessel to produce:
      a second oxygenate outlet stream from the separation vessel and comprising a substantial portion of the oxygenate from the oxygenate outlet stream; and
      a separation outlet stream from the separation vessel and comprising a substantial portion of the derivative salt from the oxygenate outlet stream.

5. The method of claim 4, further comprising recycling a portion of the separation outlet stream to the separation vessel.

6. The method of claim 4, further comprising introducing ethyl acetate to the separation vessel.

7. The method of claim 5, wherein the quench outlet stream comprises at least a substantial portion of the carbon-based oxide, the unreacted alkane, and the alkene that are present in the ODH outlet stream, and wherein the recycling comprises recycling the portion of the separation outlet stream as a recycle stream to the separation vessel via a recycle line coupled to a recycle inlet of the separation vessel and coupled to an outlet line from the separation vessel conveying the separation outlet stream.

8. The method of claim 4, wherein the carbon-based oxide comprises at least one of carbon monoxide or carbon dioxide, and wherein the separation vessel comprises a liquid-liquid extraction tower.

9. The method of claim 1, wherein the carbon-based oxide comprises carbon dioxide, and the method further comprises introducing the quench outlet stream to an amine wash tower and removing a substantial portion of the carbon-based oxide from the quench outlet stream.

10. The method of claim 1, further comprising introducing the ODH outlet stream to an oxygen remover and removing oxygen, if present, from the stream in the oxygen remover prior to introducing the ODH outlet stream to the quench tower.

11. The method of claim 1, further comprising maintaining the pH of the quench tower in a range of the pKa of the oxygenate to the pKa of the metal salt.

12. The method of claim 11, wherein the oxygenate comprises acetic acid having a pKa of 4.7 and the metal salt comprises sodium bicarbonate having a pKa of 10.3.

13. The method of claim 1, further comprising removing a portion of the oxygenate from the ODH outlet stream prior to introducing the ODH outlet stream to the quench tower.

14. The method of claim 7, further comprising:
introducing into a caustic wash tower:
the quench outlet stream; and
a caustic agent selected from at least one of sodium hydroxide, potassium hydroxide, or ammonium hydroxide, wherein the carbon-based oxide present in the quench outlet stream contacts the caustic agent in the caustic wash tower to form the metal salt; and
removing the metal salt from the caustic wash tower via the caustic outlet stream and introducing the metal salt to the quench tower as part of the caustic outlet stream.

15. The method of claim 1, comprising processing the quench outlet stream in a caustic wash tower to give the caustic outlet stream from the caustic wash tower and comprising the metal salt, wherein the metal salt comprises at least one of sodium hydrogen sulfide, sodium bicarbonate, potassium carbonate, or ammonium bicarbonate.

16. The method of claim 1, wherein the oxygenate comprises at least one of acetic acid, acrylic acid, maleic acid, or maleic anhydride.

17. The method of claim 1, wherein the derivative salt comprises at least one of sodium acetate, potassium acetate, ammonium acetate, sodium acrylate, potassium acrylate, ammonium acrylate, sodium malonate, potassium malonate, or ammonium malonate.

18. The method of claim 1, further comprising producing the caustic outlet stream by at least one process selected from an oxidative dehydrogenation process, a cracking process, a refinery process, a paper manufacturing process, a soap manufacturing process, a detergent manufacturing process, or a food manufacturing processing.

19. The method of claim 1, wherein the lower alkane comprises ethane, propane, or a mixture thereof, wherein the alkene comprises ethylene, propylene, or a mixture thereof, and the wherein the oxygenate comprises acetic acid.

20. The method of claim 19, further comprising producing olefin derivatives from the alkene, wherein the metal salt comprises a carbonate.

21. The method of claim 20, wherein the olefin derivatives comprise at least one of a polyethylene, a polypropylene, an ethylene oxide, a propylene oxide, a polyethylene oxide, a polypropylene oxide, a thermoplastic elastomer, or a thermoplastic olefin.

22. The method of claim 21, wherein the polyethylene comprises at least one of a homopolymer of ethylene, a copolymer of ethylene and an α-olefin, a high density polyethylene (HDPE), a medium density polyethylene (MDPE), a low density polyethylene (LDPE), a linear low density polyethylene (LLDPE), or a very low density polyethylene (VLDPE).

23. A method comprising:
converting a lower alkane to an alkene in an oxidative dehydrogenation (ODH) reactor and producing from the ODH reactor an ODH outlet stream comprising the alkene, unconverted lower alkane, an oxygenate, and a carbon-based oxide;
introducing the ODH outlet stream and a caustic outlet stream having a metal salt to a quench tower and converting the oxygenate in the quench tower to a derivative salt formed from the oxygenate and the metal salt, wherein the derivative salt comprises at least one of an acetate, an acrylate, or a malonate;
removing from the quench tower a quench outlet stream comprising the alkene, the unconverted lower alkane, and the carbon-based oxide;
introducing the quench outlet stream to a caustic wash tower;
contacting the carbon-based oxide from the quench outlet stream with a caustic agent in the caustic wash tower to form the metal salt; and
removing from the caustic wash tower the caustic outlet stream that is introduced to the quench tower.

24. The method of claim 23, wherein the oxygenate is acetic acid, the metal salt is a carbonate, and the derivative salt is an acetate.

25. The method of claim 24, wherein lower alkane comprises ethane and the alkene comprises ethylene.

26. The method of claim 24, comprising removing a portion of the oxygenate from the ODH outlet stream prior to introducing the ODH outlet stream to the quench tower.

27. The method of claim 23, comprising:
removing from the quench tower an oxygenate outlet stream comprising the derivative salt and unconverted oxygenate;
introducing the oxygenate outlet stream to a separation vessel to separate the unconverted oxygenate from the derivative salt; and
producing from the separation vessel a second oxygenate outlet stream comprising the unconverted oxygenate and a separation outlet stream comprising the derivative salt.

28. The method of claim 27, wherein the separation vessel comprises a liquid-liquid extraction tower.

29. The method of claim 27, comprising recycling a portion of the separation outlet stream comprising the derivative salt to the separation vessel.

30. The method of claim 27, comprising recycling, via a recycle line, a portion of the separation outlet stream comprising the derivative salt as a recycle stream to the separation vessel, wherein the recycle line is coupled to a recycle inlet of the separation vessel and coupled to an outlet line from the separation vessel conveying the separation outlet stream.

31. The method of claim 23, wherein the oxygenate comprises acetic acid and the metal salt comprises sodium bicarbonate.

32. The method of claim 23, wherein the lower alkane comprises at least one of ethane or propane, wherein the alkene comprises at least one of ethylene or propylene, and wherein the caustic agent comprises at least one of sodium hydroxide, potassium hydroxide, or ammonium hydroxide.

33. The method of claim 32, wherein the metal salt comprises at least one of sodium bicarbonate, potassium carbonate, or ammonium bicarbonate, and wherein the carbon-based oxide comprises at least one of carbon monoxide or carbon dioxide.

34. The method of claim 33, wherein the oxygenate comprises at least one of acetic acid, acrylic acid, maleic acid, or maleic anhydride, and wherein the derivative salt comprises at least one of sodium acetate, potassium acetate, ammonium acetate, sodium acrylate, potassium acrylate, ammonium acrylate, sodium malonate, potassium malonate, or ammonium malonate.

35. A method comprising:
converting a lower alkane to an alkene in an oxidative dehydrogenation (ODH) reactor and producing from the ODH reactor an ODH outlet stream comprising the alkene, unconverted lower alkane, an oxygenate, and a carbon-based oxide;
quenching the ODH outlet stream in a quench tower with a quenching agent comprising a caustic outlet stream having a metal salt, thereby converting the oxygenate to a derivative salt formed from the oxygenate and the metal salt;

removing from the quench tower a quench outlet stream comprising the alkene, the unconverted lower alkane, and the carbon-based oxide; and contacting the quench outlet stream with a caustic agent in a caustic wash tower, thereby forming the metal salt from the caustic agent and the carbon-based oxide from the quench outlet stream, wherein the caustic outlet stream having the metal salt is provided from the caustic wash tower to the quench tower.

36. The method of claim 35, wherein the oxygenate is acetic acid, the metal salt is a carbonate, and the derivative salt is an acetate.

37. The method of claim 35, comprising:

introducing an oxygenate outlet stream from the quench tower to a separation vessel, the oxygenate outlet stream comprising unconverted oxygenate and the derivative salt;

separating, via the separation vessel, the derivative salt from the unconverted oxygenate; and producing from the separation vessel a second oxygenate outlet stream comprising the unconverted oxygenate and a separation outlet stream comprising the derivative salt.

38. The method of claim 37, wherein the separation vessel comprises a liquid-liquid extraction tower.

39. The method of claim 37, comprising recycling a portion of the separation outlet stream comprising the derivative salt to the separation vessel, wherein the derivative salt comprises at least one of an acetate, an acrylate, or a malonate.

40. The method of claim 39, wherein the lower alkane comprises at least one of ethane or propane, wherein the alkene comprises at least one of ethylene or propylene, and wherein the caustic agent comprises at least one of sodium hydroxide, potassium hydroxide, or ammonium hydroxide.

41. The method of claim 35, wherein the metal salt comprises at least one of sodium bicarbonate, potassium carbonate, or ammonium bicarbonate, and wherein the derivative salt comprises at least one of sodium acetate, potassium acetate, ammonium acetate, sodium acrylate, potassium acrylate, ammonium acrylate, sodium malonate, potassium malonate, or ammonium malonate.

42. The method of claim 35, wherein the oxygenate comprises at least one of acetic acid, acrylic acid, maleic acid, or maleic anhydride, and wherein the carbon-based oxide comprises at least one of carbon monoxide or carbon dioxide.

* * * * *